US012727828B2

(12) United States Patent
Lee et al.

(10) Patent No.: US 12,727,828 B2
(45) Date of Patent: Sep. 8, 2026

(54) ELECTRONIC DEVICE FOR MEASURING BIOMETRIC SIGNAL AND METHOD OF OPERATING THE SAME

(71) Applicant: Samsung Electronics Co., Ltd., Suwon-si (KR)

(72) Inventors: Minhyoung Lee, Suwon-si (KR); Doyoon Kim, Suwon-si (KR); Moorim Kim, Suwon-si (KR); Sungyoon Kang, Suwon-si (KR); Jaekyum Lee, Suwon-si (KR); Sungjun Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 280 days.

(21) Appl. No.: 18/500,925

(22) Filed: Nov. 2, 2023

(65) Prior Publication Data

US 2024/0148330 A1 May 9, 2024

Related U.S. Application Data

(63) Continuation of application No. PCT/KR2023/016752, filed on Oct. 26, 2023.

(30) Foreign Application Priority Data

Nov. 3, 2022 (KR) ........................ 10-2022-0145191

(51) Int. Cl.
*A61B 5/00* (2006.01)
*G01S 7/282* (2006.01)
(Continued)

(52) U.S. Cl.
CPC ............ *A61B 5/6898* (2013.01); *G01S 7/282* (2013.01); *G01S 7/4021* (2013.01); *G01S 13/0209* (2013.01); *G01S 13/88* (2013.01)

(58) Field of Classification Search
CPC ..... A61B 5/6898; G01S 7/282; G01S 7/4021; G01S 13/0209; G01S 13/88
See application file for complete search history.

(56) References Cited

U.S. PATENT DOCUMENTS

| | | | |
|---|---|---|---|
| 11,925,447 B1 * | 3/2024 | Patel | G01S 13/723 |
| 2015/0105631 A1 | 4/2015 | Tran et al. | |

(Continued)

FOREIGN PATENT DOCUMENTS

| | | |
|---|---|---|
| JP | 2016077890 A | 5/2016 |
| JP | 2021175455 A | 11/2021 |

(Continued)

OTHER PUBLICATIONS

Search Report and Written Opinion dated Jan. 17, 2024 issued in International Patent Application No. PCT/KR2023/016752.

(Continued)

*Primary Examiner* — Nazra Nur Waheed
(74) *Attorney, Agent, or Firm* — NIXON & VANDERHYE P.C.

(57) ABSTRACT

Disclosed is an electronic device comprising: a sensor module, a communication circuit, and at least one processor. The at least one processor may be configured to: identify a mounting state of the electronic device based on sensor data received from the sensor module, select at least one antenna combination including at least one transmission antenna and at least one reception antenna from among the one or more antennas according to the mounting state, obtain a radar signal related to a measurement target from the communication circuit through the at least one antenna combination, obtain a biometric signal from the obtained radar signal, evaluate a signal quality of the biometric signal, and adjust control parameters for an antenna combination selected from among the at least one antenna combination according to the (Continued)

sensor data, the radar signal, and the signal quality of the biometric signal.

20 Claims, 29 Drawing Sheets

(51) Int. Cl.

| | |
|---|---|
| ***G01S 7/40*** | (2006.01) |
| ***G01S 13/02*** | (2006.01) |
| ***G01S 13/88*** | (2006.01) |

(56) References Cited

U.S. PATENT DOCUMENTS

| | | | | |
|---|---|---|---|---|
| 2016/0100766 | A1 | 4/2016 | Yoshioka et al. | |
| 2018/0262248 | A1 | 9/2018 | Zou | |
| 2019/0393944 | A1 | 12/2019 | Huang et al. | |
| 2020/0237252 | A1* | 7/2020 | Lane | G01S 13/88 |
| 2020/0264299 | A1* | 8/2020 | Viberg | F21V 33/0052 |
| 2022/0047208 | A1* | 2/2022 | Shin | A61B 5/11 |
| 2022/0173793 | A1 | 6/2022 | Byun et al. | |
| 2023/0273309 | A1 | 8/2023 | Kang et al. | |
| 2023/0405263 | A1* | 12/2023 | Gartenberg | A61B 5/6892 |
| 2024/0053466 | A1* | 2/2024 | Naka | G01S 13/06 |

FOREIGN PATENT DOCUMENTS

| | | | |
|---|---|---|---|
| JP | 2022021422 | A | 2/2022 |
| KR | 10-2017-0055352 | | 5/2017 |
| KR | 20180032980 | A | 4/2018 |
| KR | 10-2019-0079060 | | 7/2019 |
| KR | 10-2019-0110305 | | 9/2019 |
| KR | 10-2021-0027993 | | 3/2021 |
| KR | 20220022606 | A | 2/2022 |
| KR | 10-2381262 | | 4/2022 |
| KR | 10-2022-0063862 | | 5/2022 |
| WO | 2022046072 | A1 | 3/2022 |

OTHER PUBLICATIONS

Extended European Search Report dated Nov. 13, 2025 issued in European Patent Application No. 23886135.5, 10 pp.

* cited by examiner

1002

Radar signal preprocessing

Carrier removal

Clutter removal (Dynamic)

Differential

1004

Measure distance measurement using radar signal

D. ^2

Smoothing(moving average filter)
& Normalization

Determine target position range

Magnitude of radar signal by TX power (pwidx)

1410

Respiration signal by sampling rate

1420

1710

ANT1/2/3
- Directional antenna
- High TX/RX performance
- Rear mounting
- Rear mounting only available
- Front mounting is incapable of radiation due to display

1720

ANT0/4
- Omnidirectional antenna
- Low TX/RX performance
- Side mounting
- Omnidirectional mounting available

ELECTRONIC DEVICE FOR MEASURING BIOMETRIC SIGNAL AND METHOD OF OPERATING THE SAME

CROSS-REFERENCE TO RELATED APPLICATIONS

This application is a continuation of International Application No. PCT/KR2023/016752 designating the United States, filed on Oct. 26, 2023, in the Korean Intellectual Property Receiving Office and claiming priority to Korean Patent Application No. 10-2022-0145191, filed on Nov. 3, 2022, in the Korean Intellectual Property Office, the disclosures of each of which are incorporated by reference herein in their entireties.

BACKGROUND

Field

The disclosure relates to an electronic device for measuring a biometric signal and a method for operating the same.

Description of Related Art

Ultra-wideband (UWB) communication technology may transmit massive information with a relatively low spectral power density over a wide frequency band as compared to conventional wireless communication technology. UWB may refer to a wireless transmission technology that has an occupied bandwidth of 20% or more of the center frequency or occupies an occupied bandwidth of 500 MHz or more. UWB uses signals with a bandwidth of 500 MHz and a very short pulse width of several nano seconds (ns) in the 3.1 GHz to 10.6 GHz frequency band and may thus be robust to noise. Further, as using a double-sided two-way ranging (DS-TWR) method, UWB may be used for ranging with high accuracy in centimeter (cm) units.

An electronic device including a UWB radar may obtain a UWB radar signal and a biometric signal using all combinations of transmission antennas and reception antennas regardless of the mounting state of the electronic device. The mounting state of the electronic device may be limited so that the electronic device is able to obtain UWB radar signals with good signal quality when receiving UWB radar signals through the UWB radar. For example, the electronic device may receive UWB radar signals only when it is in a designated, specific mounting state.

SUMMARY

Embodiments of the disclosure provide an electronic device for measuring a biometric signal in a contactless manner based on a UWB radar and a method for operating the same.

Embodiments of the disclosure provide an electronic device that obtains a UWB radar signal and a biometric signal regardless of the mounting state of the electronic device and a method for operating the same.

An electronic device according to an example embodiment may comprise: a sensor module including at least one sensor, a communication circuit including one or more antennas configured to support ultra-wideband (UWB) communication, and at least one processor operatively coupled with the sensor module and the communication circuit. The at least one processor may be configured to identify a mounting state of the electronic device based on sensor data received from the sensor module. The at least one processor may be configured to select at least one antenna combination including at least one transmission antenna and at least one reception antenna from among the one or more antennas according to the mounting state; The at least one processor may be configured to obtain a radar signal related to a measurement target from the communication circuit through the at least one antenna combination. The at least one processor may be configured to obtain a biometric signal from the obtained radar signal. The at least one processor may be configured to evaluate a signal quality of the biometric signal. The at least one processor may be configured to adjust control parameters for an antenna combination selected from among the at least one antenna combination according to the sensor data, the radar signal, and the signal quality of the biometric signal.

A method for operating an electronic device according to an example embodiment may comprise identifying a mounting state of the electronic device based on sensor data received from a sensor module. The method may comprise selecting at least one antenna combination including at least one transmission antenna and at least one reception antenna from among one or more antennas included in an ultra-wideband (UWB) communication circuit according to the mounting state. The method may comprise obtaining a radar signal related to a measurement target from the UWB communication circuit through the at least one antenna combination. The method may comprise obtaining a biometric signal from the obtained radar signal. The method may comprise evaluating a signal quality of the biometric signal. The method may comprise adjusting control parameters for an antenna combination selected from among the at least one antenna combination according to the sensor data, the radar signal, and the signal quality of the biometric signal.

A non-transitory computer-readable storage medium storing one or more programs according to an example embodiment, the one or more programs may include instructions that, when executed by at least one processor of an electronic device, cause the electronic device to: identify a mounting state of the electronic device based on sensor data received from a sensor module, select at least one antenna combination including at least one transmission antenna and at least one reception antenna from among one or more antennas included in an ultra-wideband (UWB) communication circuit according to the mounting state, obtain a radar signal related to a measurement target from the UWB communication circuit through the at least one antenna combination, obtain a biometric signal from the obtained radar signal, evaluate a signal quality of the biometric signal, and adjust control parameters for an antenna combination selected from among the at least one antenna combination according to the sensor data, the radar signal, and the signal quality of the biometric signal.

BRIEF DESCRIPTION OF THE DRAWINGS

The above and other aspects, features and advantages of certain embodiments of the present disclosure will be more apparent from the following detailed description, taken in conjunction with the accompanying drawings, in which.

DETAILED DESCRIPTION

Figure 1:
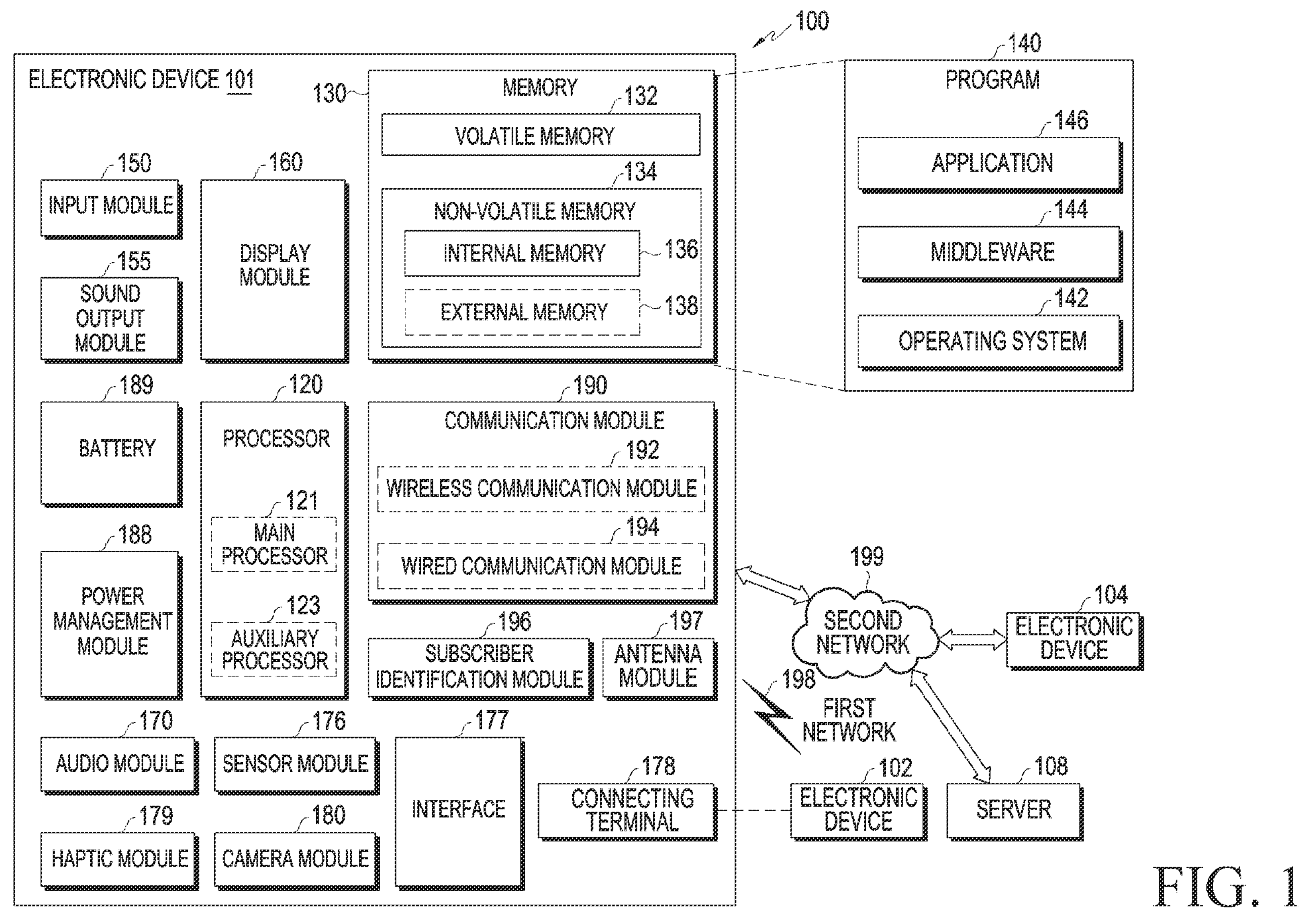
FIG. 1 is a diagram illustrating an example electronic device in a network environment according to various embodiments.

FIG. 1 is a block diagram illustrating an example electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In an embodiment, at least one (e.g., the connecting terminal 178) of the components may be omitted from the electronic device 101, or one or more other components may be added in the electronic device 101. According to an embodiment, some (e.g., the sensor module 176, the camera module 180, or the antenna module 197) of the components may be integrated into a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to an embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be configured to use lower power than the main processor 121 or to be specified for a designated function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. The artificial intelligence model may be generated via machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, keys (e.g., buttons), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display 160 may include, for example, a display, a hologram device, or a projector and control circuitry to control a corresponding one of the display, hologram device, and projector. According to an embodiment, the display 160 may include a touch sensor configured to detect a touch, or a pressure sensor configured to measure the intensity of a force generated by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an accelerometer, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via a first network 198 (e.g., a short-range communication network, such as Bluetooth™, wireless-fidelity (Wi-Fi) direct, or infrared data association (IrDA)) or a second network 199 (e.g., a long-range communication network, such as a legacy cellular network, a 5G network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device). According to an embodiment, the antenna module 197 may include one antenna including a radiator formed of a conductive body or conductive pattern formed on a substrate (e.g., a printed circuit board (PCB)). According to an embodiment, the antenna module 197 may include a plurality of antennas (e.g., an antenna array). In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, instructions or data may be transmitted or received between the electronic device 101 and the external electronic device 104 via the server 108 coupled with the second network 199. The external electronic devices 102 or 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment, the external electronic device 104 may include an Internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or health-care) based on 5G communication technology or IoT-related technology.

Figure 2:
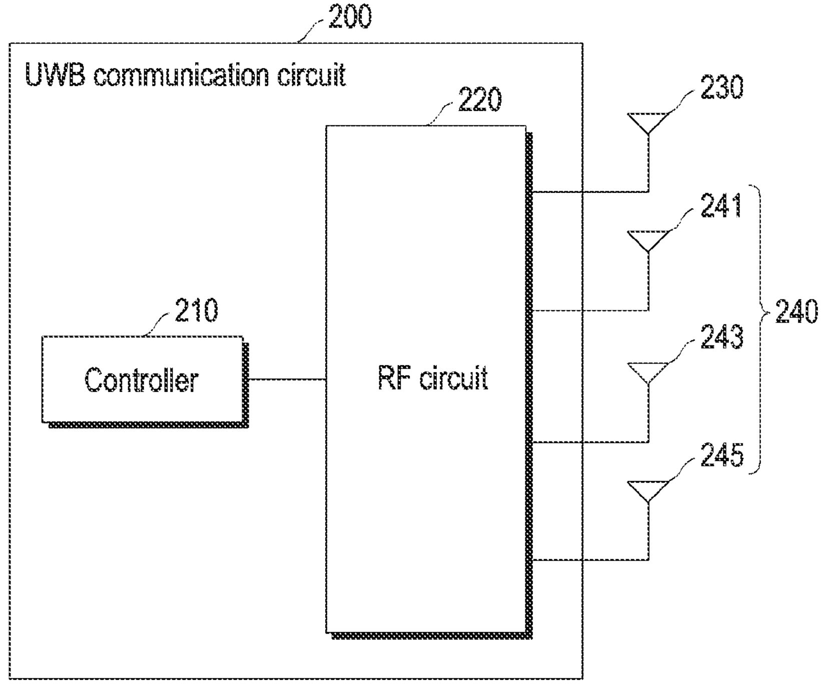
FIG. 2 is a block diagram illustrating an example configuration of a UWB communication circuit according to various embodiments.

FIG. 2 is a block diagram illustrating an example configuration of a UWB communication circuit 200 according to various embodiments.

Referring to FIG. 2, an ultra-wide band (UWB) communication circuit 200 includes a controller (e.g., including control/processing circuitry) 210, a radio frequency (RF) circuit 220 connected to the controller 210, at least one distance ranging antenna 230 connected to the RF circuit 220, and one or more angle of arrival (AoA) ranging antennas 240 (241, 243, and 245) connected to the RF circuit 220.

In an embodiment, the UWB communication circuit 200 may be included in the wireless communication module 192 of the electronic device 101, or may be electrically connected with the electronic device 101 as hardware independent from the wireless communication module 192. In an embodiment, at least a portion (e.g., the RF circuit 220 and/or the antennas 230 and 240) of the UWB communication circuit 200 may be included in the electronic device 101.

In an embodiment, the UWB communication circuit 200 may perform a ranging operation of recognizing a measurement target (not shown) (e.g., an external object such as a person) based on UWB communication. In an embodiment, the ranging operation may include a distance ranging operation and an AoA ranging operation. The distance ranging operation may include an operation of measuring the distance between the UWB communication circuit 200 and the measurement target. The distance ranging operation may be performed based on time of flight (ToF) measurement using the distance ranging antenna 230, but is not limited thereto. The AoA ranging operation may include an operation of identifying an AOA of a signal reflected from the measurement target and received by the UWB communication circuit 200 or a signal transmitted by the measurement target (e.g., an external electronic device). The AoA ranging operation may be performed based on a difference between reception time points of signals at the plurality of AoA ranging antennas 241, 243, and 245, but is not limited thereto.

In an embodiment, the controller 210 may include a processing circuit controlling the RF circuit 220 to perform a ranging operation based on the at least one distance ranging antenna 230 or any one of the one or more AoA ranging antennas 240. In an embodiment, the controller 210 of the UWB communication circuit 200 may be configured independently of the processor 120 of the electronic device 101 or may be implemented as a part of the processor 120 of the electronic device 101. An operation in which the controller 210 of the UWB communication circuit 200 or the processor 120 of the electronic device 101 controls the RF circuit 220 and the ranging antennas 230 and 240 may be described in the following embodiments.

In an embodiment, the RF circuit 220 may generate an RF signal based on the control signal received from the controller 210. The RF circuit 220 may transfer the RF signal to the at least one distance ranging antenna 230 and/or may process the RF signal output from the distance ranging antenna 230 and may transfer the RF signal to the controller 210. The controller 210 may perform a distance ranging operation based on the control of the RF circuit 220. In an embodiment, the one or more AoA ranging antennas 240 may receive the RF signal based on detecting a change in the electromagnetic field around the UWB communication circuit 200. The RF circuit 220 may transfer an RF signal to be transmitted to any one of the one or more AoA ranging antennas 240, and/or may process RF signals received through the AoA ranging antennas 240. The controller 210 may perform a distance ranging operation or an AoA ranging operation based on the control of the RF circuit 220 described above. In an embodiment, the RF circuit 220 may process an RF signal output from the at least one distance ranging antenna 230 or the one or more AoA ranging antennas 240, may convert the RF signal into a baseband signal, and may transfer the baseband signal to the controller 210.

In an embodiment, the at least one distance ranging antenna 230 may be used for a distance ranging operation. The at least one distance ranging antenna 230 may receive an RF signal based on detecting a change in the electromagnetic field around the UWB communication circuit 200. The RF signal received by the at least one ranging antenna 230 may include, e.g., a high frequency signal of 3.5 GHz or more. The at least one distance ranging antenna 230 may transfer the received RF signal to the RF circuit 220. The number of the at least one range antenna 230 is not limited to that illustrated in FIG. 2. For example, the UWB communication circuit 200 may include one or more distance range antennas 230. In an embodiment, at least one of the one or more distance ranging antennas 230 may be implemented as a "metal antenna".

In an embodiment, the one or more AoA ranging antennas 240 may be used for an AoA ranging operation. The one or more AoA ranging antennas 240 may include at least one of a first AoA ranging antenna 241, a second AoA ranging antenna 243, or a third AoA ranging antenna 245. The one or more AoA ranging antennas 240 may receive RF signals of a high frequency band. RF signals received by the one or more AoA ranging antennas 240 may include, e.g., signals of a frequency of 3.5 GHz or more. The one or more AoA ranging antennas 240 may transfer the received RF signals to the RF circuit 220. In an embodiment, at least one of the one or more AoA ranging antennas 241, 243, and 245 may be implemented as a "patch antenna".

Although FIG. 2 illustrates that the UWB communication circuit 200 includes the controller 210, the RF circuit 220, the at least one distance ranging antenna 230, and the one or more AoA ranging antennas 240, the components included in the UWB communication circuit 200 are not limited to those illustrated. For example, the UWB communication circuit 200 may further include at least one component illustrated in FIG. 1. For example, the UWB communication circuit 200 may be included in at least one component illustrated in FIG. 1.

In an embodiment, the UWB communication circuit 200 may collect a radar signal (e.g., a UWB radar signal) within a radar field of view (FOV). In an embodiment, the UWB communication circuit 200 may transmit a signal (e.g., a signature signal) of a specific format through at least one of the at least one distance ranging antenna 230 and the one or more AoA ranging antennas 240. The UWB communication circuit 200 may collect the radar signal (e.g., a UWB radar signal) which is the transmitted signal reflected from the measurement target (e.g., an external object such as a person) and returned by at least one of the at least one distance ranging antenna 230 and the one or more AoA ranging antennas 240.

The UWB communication circuit 200 may measure the time when the radar signal arrives after the signal of the specific format is transmitted, and may calculate the distance between the UWB communication circuit 200 and the object as in, e.g., the following equation.

Distance between UWB communication circuit 200 and object=speed of radio wave*time when signal is reflected and returned/2

Speed of radio wave in the air=speed C of light

In an embodiment, the signal transmitted from the UWB communication circuit 200 may be reflected after reaching an external object (e.g., an object or a person) positioned within the radar field of view, and the UWB communication circuit 200 may receive the reflected signal (e.g., referred to as a radar signal). Among the transmitted signals, the signal in the area that does not touch the external object may be continuously radiated while only the signal in the area that touches the external object may be reflected. Some of the radar signals that touch some objects (e.g., humans or animals) may be transmitted. Using this property, the electronic device (e.g., the controller 210 or the processor 120) may extract a biometric signal (e.g., respiration and/or heart rate) of an external object (a person or an animal) from the radar signal.

In an embodiment, signals transmitted and received based on UWB communication technology may refer, for example, to signals having a bandwidth greater than a designated center frequency or signals having a bandwidth greater than 0.5 GHz, for example. In an example, the signals may be specified in a band of 3.1 GHz to 10.6 GHz. The UWB communication circuit 200 may generate very short RF pulses in a range of less than nanoseconds and use them for sensing objects and image applications.

In an embodiment, each of the at least one distance ranging antenna 230 or the one or more AoA ranging antennas 240 of the UWB communication circuit 200 may operate as a UWB radar and/or a UWB radar sensor. The UWB communication circuit 200 may periodically transmit a signal (e.g., a signature signal) having a given signature pulse through at least one distance ranging antenna 230 or one or more AoA ranging antennas 240 operating as a UWB radar.

The radar signal received through the at least one distance ranging antenna 230 or the one or more AoA ranging antennas 240 operating as the UWB radar sensor may pass through a high pass filter (HPF), a low noise amplifier (LNA), and a mixer in the RF circuit 220, be sampled, and then stored in a buffer (e.g., a frame buffer). Each of the sampled data may indicate where the radar signal is reflected away from the UWB communication circuit 200. The electronic device 101 (e.g., the processor 120 or the controller 210) may analyze the collected radar signals to extract biometric signals indicating life signs (e.g., movement, heart rate, and/or respiration) of an object (e.g., a living object) present in the radar field of view.

Figure 3:
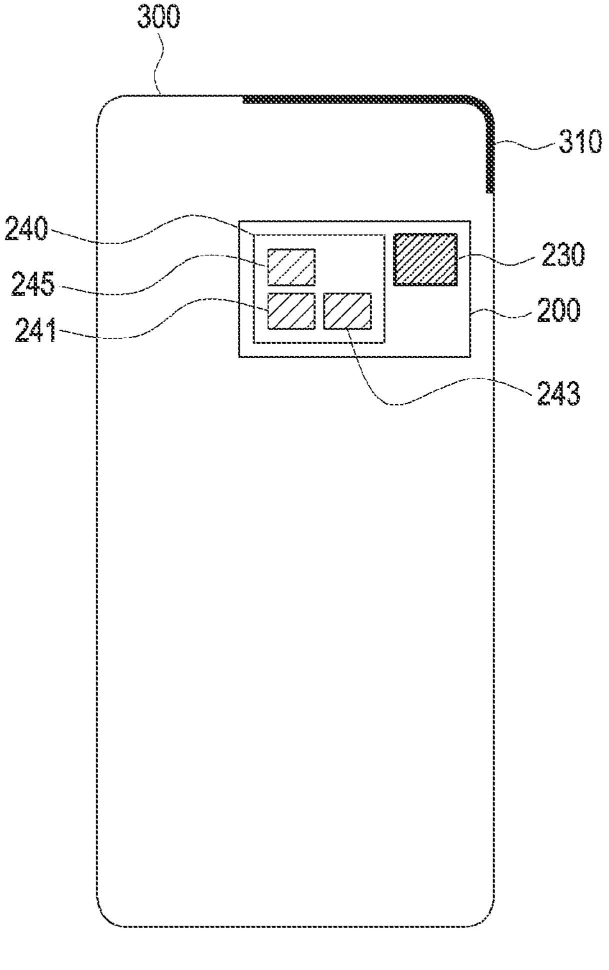
FIG. 3 is a diagram illustrating an arrangement of antennas included in a housing of an electronic device according to various embodiments.

FIG. 3 is a diagram illustrating an example arrangement of antennas 230 and 240 included in a housing 300 of an electronic device (e.g., the electronic device 101 of FIG. 1) according to various embodiments.

Referring to FIG. 3, the UWB communication circuit 200 may be contained in the housing 300, and/or at least a portion thereof may be disposed on the housing 300, and the placement position thereof is not limited thereto. In an embodiment, the cellular antenna 310 may be disposed on the housing 300 of the electronic device 101 or may be contained in the housing 300, but the placement position thereof is not limited thereto. The cellular antenna 310 may receive a cellular signal for cellular communication (e.g., 3G, 4G, or 5G communication, but is not limited thereto).

In an embodiment, at least one of the at least one distance ranging antenna 230 of the UWB communication circuit 200 may be disposed closer to a side surface of the housing 300 than the one or more AoA ranging antennas 340. In an embodiment, at least one of the one or more AoA ranging antennas 240 of the UWB communication circuit 200 may be mounted at a position farther from the side surface of the housing 300 than the at least one distance ranging antenna 330. In an embodiment, when the cellular antenna 310 transmits and/or receives a signal of a designated frequency, the UWB communication circuit 200 may perform a distance ranging operation based on the at least one AoA ranging antenna 230, thereby reducing the degree of deterioration of the distance ranging performance.

In an embodiment, each of the at least one distance ranging antenna 230 and the one or more AoA ranging antennas 340 may operate as a transmission antenna, a reception antenna, or a transmission-cum-reception antenna. To accurately measure the biometric signal from the radar signal, the UWB communication circuit 200 may use the combination (e.g., an antenna combination) of at least one transmission antenna and at least one reception antenna directed toward the measurement target (not shown). A mount capable of mounting the electronic device 101 including the UWB communication circuit 200 may be used to allow the antenna combination to be directed toward the measurement target, or the electronic device 101 including the UWB communication circuit 200 may be mounted on the ceiling or at a fixed position.

Figure 4A:
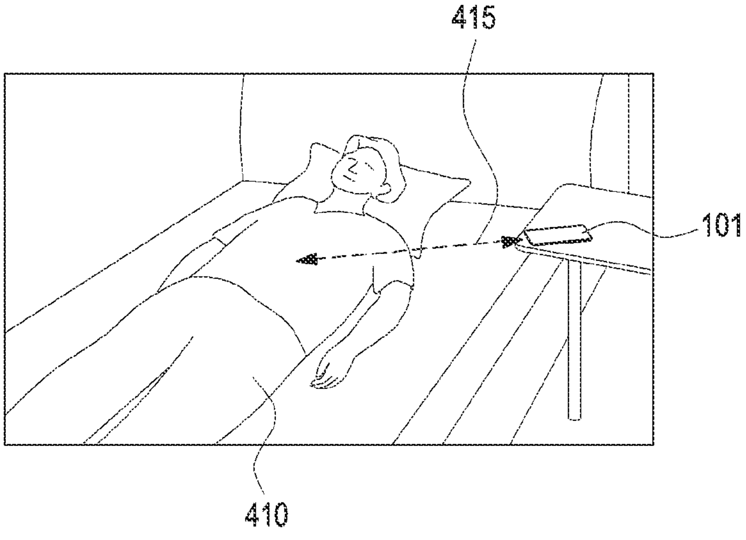
FIG. 4A is a diagram illustrating an example of UWB measurement using a fixedly installed UWB communication circuit according to various embodiments.

FIG. 4A is a diagram illustrating an example of UWB measurement using a fixedly installed UWB communication circuit according to various embodiments.

Referring to FIG. 4A, an electronic device 101 (e.g., the electronic device 101 including the UWB communication circuit 200) may be fixedly installed on a ceiling, a wall, or a shelf to face a measurement target 410 (e.g., a person lying on a bed). The electronic device 101 may receive a radar signal reflected from the measurement target 410 within the measurement distance 415 corresponding to the radar field of view and extract a biometric signal of the measurement target 410 from the radar signal.

Figure 4B:
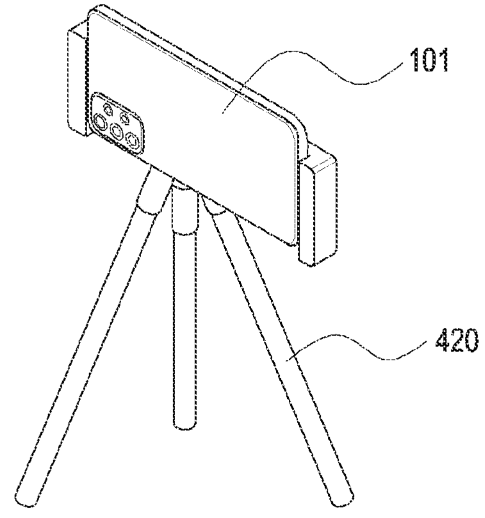
FIG. 4B is a diagram illustrating an example of UWB measurement using a UWB communication circuit on a mount according to various embodiments.

FIG. 4B is a diagram illustrating an example of UWB measurement using a UWB communication circuit on a mount according to various embodiments.

Referring to FIG. 4B, the electronic device 101 (e.g., the electronic device 101 including the UWB communication circuit 200) may be mounted on a mount 420 such as a tripod, and the user may move the mount 420 or the electronic device 101 on the mount 420 such that the electronic device 101 (e.g., the antennas 230 and 240) faces the measurement target (not shown).

The fixedly installing of FIG. 4A or the use of a mount of FIG. 4B requires a separate device (a fixing bracket or a mount 420) to install or mount the UWB communication circuit 200 and may render it difficult for the user to determine an accurate position for obtaining a UWB signal of good quality. Further, such ways may not precisely measure the biometric signal or analyze the state of the measurement target because the signal quality of the UWB signal varies depending on the posture, position, and/or direction of the measurement target (e.g., a person) during measurement.

According to embodiments of the disclosure, to obtain UWB signals, the electronic device 101 (e.g., the electronic device 101 including the UWB communication circuit 200) including multiple antennas (e.g., at least one distance ranging antenna 230 and one or more AoA ranging antennas 240) may select an antenna combination according to the position and the mounting state of the electronic device 101 and collect radar signals through the selected antenna combination. Various example embodiments described below may obtain a radar signal having good signal quality in various mounting situations of the electronic device 101. The embodiments described below may track, in real-time, the variation in signal quality according to the change in the position and/or posture of the measurement target during measurement, select an antenna combination and/or parameters for use in the antenna combination, and obtain radar signals of good quality through the selected antenna combination and/or control parameters.

Figure 5:
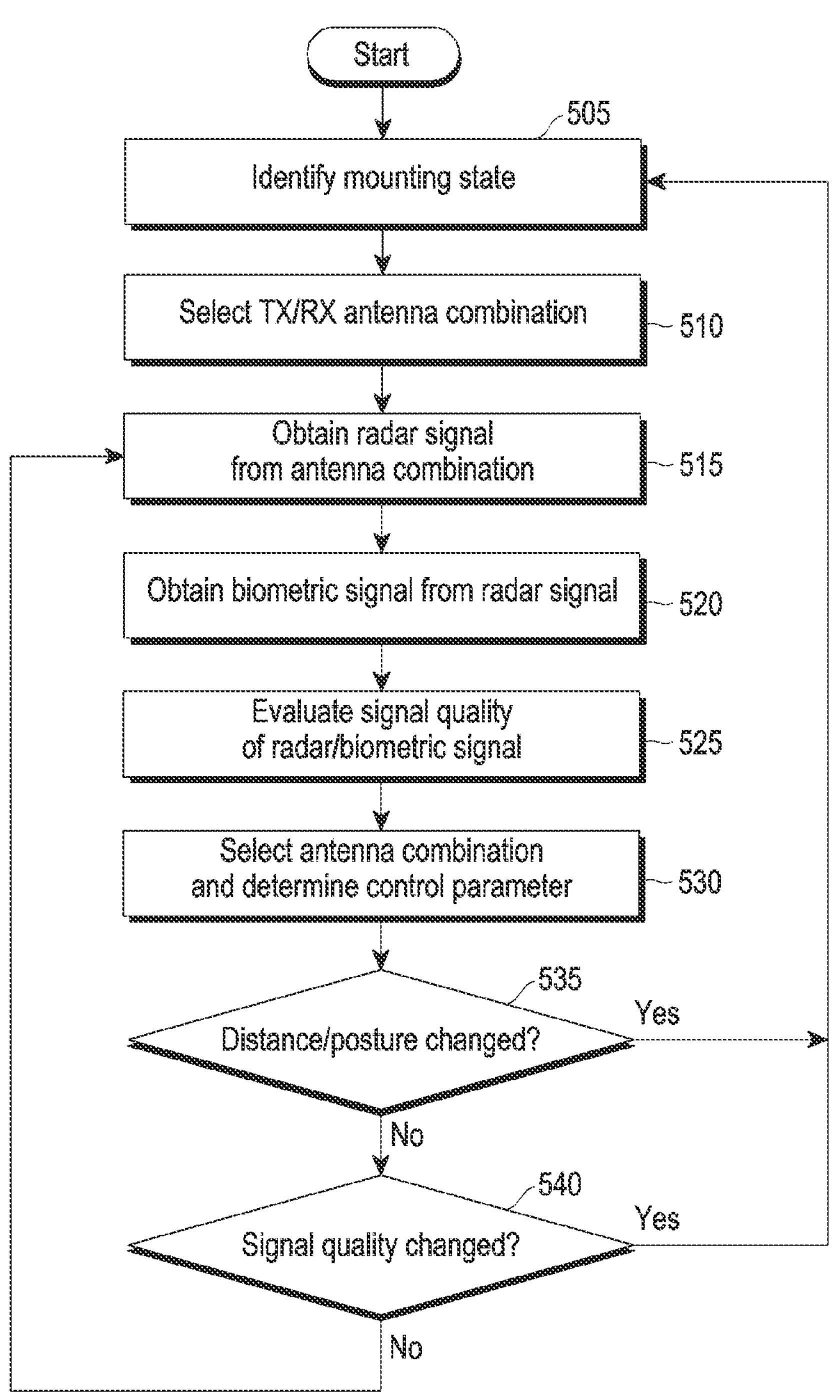
FIG. 5 is a flowchart illustrating an example procedure for measuring a UWB-based biometric signal according to various embodiments.

FIG. 5 is a flowchart illustrating an example procedure for measuring a UWB-based biometric signal according to various embodiments. At least one of operations to be described below may be executed by the electronic device 101 (e.g., the processor 120).

According to embodiments, at least one of operations to be described below may be omitted, modified, or ordered.

Referring to FIG. 5, in operation 505, the electronic device 101 (e.g., the processor 120) may identify the mounting state of the electronic device 101 (e.g., the electronic device 101 including the UWB communication circuit 200). In an embodiment, the electronic device 101 (e.g., the processor 120) may identify the mounting state of the electronic device 101 using an acceleration sensor, a gyro sensor, and/or a proximity sensor included in a sensor module (e.g., the sensor module 176) of the electronic device 101 and a camera module (e.g., the camera module 180) of the electronic device 101. In an embodiment, the mounting state may indicate the direction in which the electronic device 101 (e.g., the antennas 230 and 240 of the UWB communication circuit 200) faces the measurement target. In an embodiment, the mounting state may include a mounting type and/or a mounting angle of the electronic device 101.

Figure 6A:
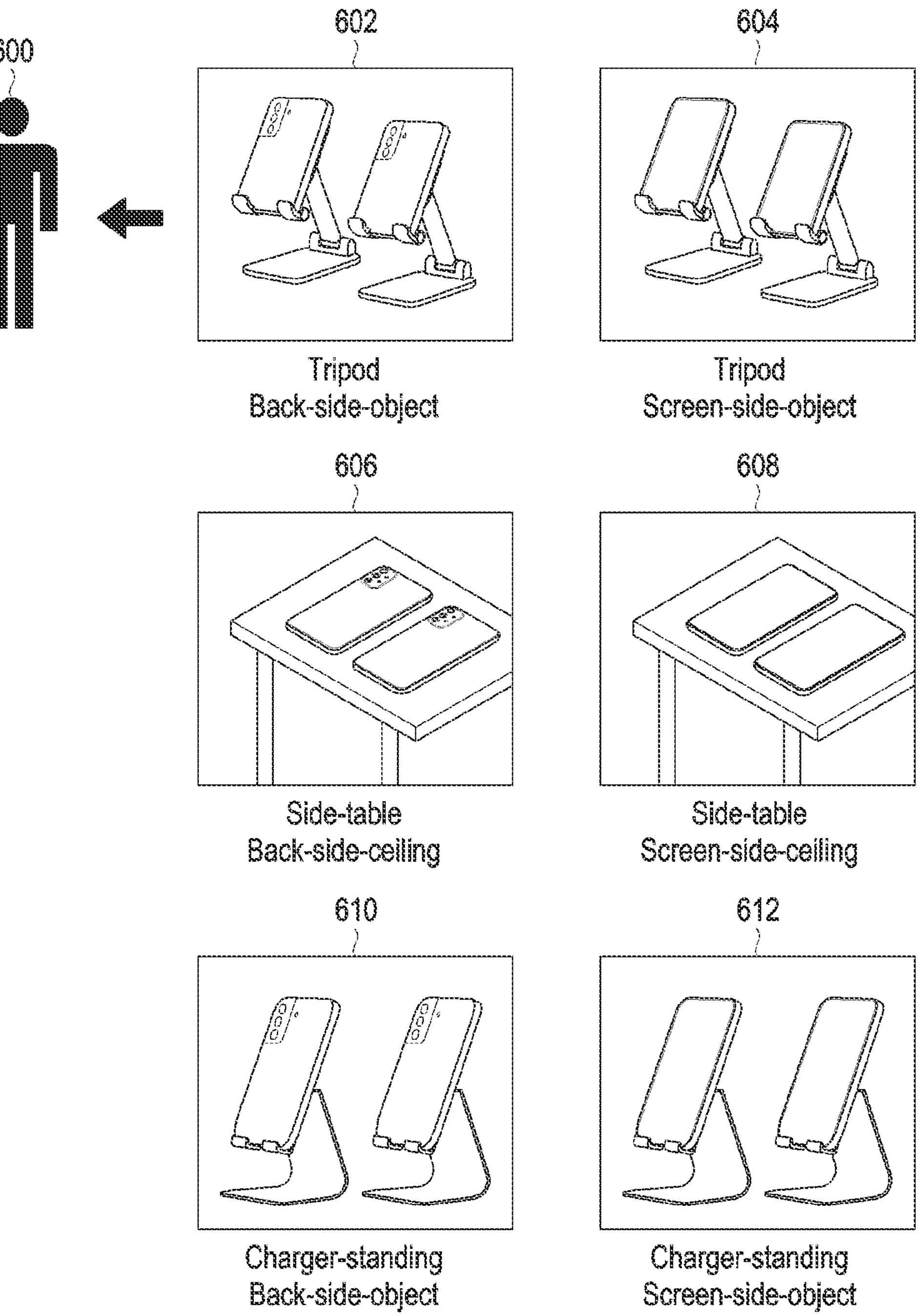
FIG. 6A is a diagram illustrating various example mounting types of an electronic device according to various embodiments.

In an embodiment, the electronic device 101 (e.g., the processor 120) may identify the mounting type (e.g., any one of the mounting types 602, 604, 606, 608, 610, and 612 of FIG. 6A) of the electronic device 101 based on sensor data collected from an acceleration sensor, a gyro sensor, and/or a proximity sensor included in the sensor module 176 and sensor data collected from the camera module 180.

In an embodiment, the electronic device 101 (e.g., the processor 120) may identify the mounting angle (e.g., the mounting angles 622 and 624 of FIG. 6B) indicating the direction in which the electronic device 101 (e.g., the antennas 230 and 240 of the UWB communication circuit 200) faces the measurement target, based on sensor data collected from the acceleration sensor, the gyro sensor, and/or the proximity sensor included in the sensor module 176 and sensor data collected from the camera module 180.

In operation 510, the electronic device 101 (e.g., the processor 120) may select at least one antenna combination based on the mounting state. In an embodiment, each antenna combination may include at least one transmission antenna and at least one reception antenna directed toward the measurement target. In an embodiment, at least one transmission antenna of each antenna combination may include at least one of the at least one distance ranging antenna 230 or the one or more AoA ranging antennas 240. In an embodiment, at least one reception antenna of each antenna combination may include at least one of the at least one distance ranging antenna 230 or the one or more AoA ranging antennas 240.

In an embodiment, the UWB communication circuit 200 may include one or more metal antennas (e.g., the distance ranging antennas 230) (e.g., the ANT0 701 and the ANT4 709 of FIG. 7A) disposed relatively close to the side surface of the housing (e.g., the housing 300) of the electronic device 101, and one or more patch antennas (e.g., the AoA ranging antennas 240) (e.g., the ANT1 703, the ANT2 705, and the ANT3 707 of FIG. 7A) disposed on the rear surface of the housing (e.g., the housing 300) of the electronic device 101.

In an embodiment, the antenna combination may include, for example, and without limitation, {ANT1, ANT2}, {ANT1, ANT3}, {ANT0, ANT0}, {ANT0, ANT4}, {ANT4, ANT0}, and {ANT4, ANT4}. In an embodiment, the antenna combination may include one or more transmission antennas (e.g., at least one of ANT0, ANT1, or ANT4) and one or more reception antennas (e.g., at least one of ANT0, ANT2, ANT3, or ANT4).

In an embodiment, the electronic device 101 (e.g., the processor 120) may determine at least one antenna combination determined to be appropriate for collecting the radar signal from the measurement target, based on the mounting state and positions where multiple antennas (e.g., ANT0 701, ANT1 703, ANT2 705, ANT3 707, and ANT4 709) are disposed inside the electronic device 101. Embodiments related to operation 510 are described in greater detail below with reference to FIGS. 7A, 7B, 8A, and 8B.

In operation 515, the electronic device 101 (e.g., the processor 120) may obtain at least one radar signal from the selected at least one antenna combination. In an embodiment, the electronic device 101 (e.g., the processor 120) may obtain a first radar signal (e.g., the radar signal 902 of FIG. 9) from, for example, and without limitation, {ANT1 and ANT2} and a second radar signal (e.g., the radar signal 904 of FIG. 9) from, for example, and without limitation, {ANT1 and ANT3}.

In operation 520, the electronic device 101 (e.g., the processor 120) may extract at least one biometric signal (e.g., heart rate and/or respiration) from the at least one radar signal. In an embodiment, the electronic device 101 (e.g., the processor 120) may measure the distance to the measurement target based on the at least one radar signal. In an embodiment, the electronic device 101 (e.g., the processor 120) may perform preprocessing (e.g., the preprocessing 1002 of FIG. 10A) on each radar signal and may determine a range in which the measurement target is positioned by performing distance measurement (e.g., the distance measurement 1004 of FIG. 10B) using the preprocessed signal. In an embodiment, the electronic device 101 (e.g., the processor 120) may determine that a measurement target (e.g., a person) is in a sleep state, based on the at least one biometric signal (e.g., respiration and/or heart rate), and may identify the posture (e.g., the supine posture 1202, the lateral right posture 1204, the lateral left posture 1206, or the prone posture 1208 of FIG. 12A) of the measurement target in the sleep state.

In operation 525, the electronic device 101 (e.g., the processor 120) may evaluate a signal quality (e.g., a signal quality indicator (SQI)) of the at least one radar signal and/or the at least one biometric signal. In an embodiment, the signal quality may include a signal-to-noise ratio (SNR) (e.g., the first SNR 1302 or the second SNR 1304 of FIG. 13A) of the radar signal and/or the biometric signal. In an embodiment, the signal quality may include an autocorrelation value (e.g., the autocorrelation value 1314 of FIG. 13B) of the radar signal and/or the biometric signal.

In operation 530, the electronic device 101 (e.g., the processor 120) may select at least one of the at least one antenna combination based on the signal quality and may determine control parameters for the selected antenna combination. In an embodiment, the control parameters may include at least one of the number of transmission antennas, the number of reception antennas, the measurement distance, transmission power, the number of transmission pulses, the reception gain, or the sampling rate. In an embodiment, the electronic device 101 (e.g., the processor 120) may select a radar signal and/or a biometric signal of a better signal quality, adjust the control parameters to reduce current consumption of the UWB communication circuit 200, and apply the adjusted control parameters to the corresponding antenna combination. In an embodiment, the electronic device 101 (e.g., the processor 120) may select at least one antenna combination having a better signal quality and may not select at least one antenna combination having a better signal quality. Embodiments related to control parameter adjustment of operation 530 are described in greater detail below with reference to FIGS. 15, 16A, and 16B. Embodiments related to antenna combination selection of operation 530 are described in greater detail below with reference to FIGS. 17A and 17B.

In an embodiment, when the SNR of the radar signal and/or the biometric signal corresponding to any one (e.g., the first antenna combination) of the at least one antenna combination of operation 510 is low (e.g., less than a designated threshold), or when the signal acquisition rate of the biometric signal (e.g., respiration and/or heart rate) extracted from the radar signal corresponding to the first antenna combination is low (e.g., less than a designated threshold), the electronic device 101 (e.g., the processor 120) may perform at least one of the following example, non-limiting, operations:

- Increase the transmission power for the first antenna combination by a designated value (or to a designated value);
- Increase the number of transmission pulses for the first antenna combination by a designated value (or to a designated value);
- Increase the reception gain for the first antenna combination by a designated value (or to a designated value);
- Increase the sampling rate for sampling the rater signal of the first antenna combination by a designated value (or to a designated value); or
- Increase the number of transmission antennas and/or the number of reception antennas to be included in the first antenna combination by a designated value (or to a designated value).

In an embodiment, the electronic device 101 (e.g., the processor 120) may apply the control parameters (e.g., at least one of transmission power, the number of transmission pulses, reception gain, sampling rate, the number of transmission antennas, or the number of reception antennas) adjusted by performing the above-described operations to the first antenna combination, and may obtain a radar signal and/or a biometric signal having a more enhanced signal quality through the adjusted first antenna combination.

In an embodiment, when the SNR of the biometric signal extracted from the radar signal corresponding to any one (e.g., the second antenna combination) of the at least one antenna combination of operation 510 is high (e.g., greater than the designated threshold), or when the signal acquisition rate of the biometric signal (e.g., respiration and/or heart rate) extracted from the radar signal is high (e.g., greater than the designated threshold), the electronic device 101 (e.g., the processor 120) may perform at least one of the following example, non-limiting, operations:

Decrease the transmit power for the second antenna combination by a designated value (or to a designated value);

Decrease the sampling rate for the second antenna combination by a designated value (or to a designated value); or Decrease the number of transmission antennas and/or the number of reception antennas to be included in the second antenna combination by a designated value (or to a designated value).

In an embodiment, the electronic device 101 (e.g., the processor 120) may apply the control parameters (e.g., at least one of transmission power, the number of transmission pulses, reception gain, sampling rate, the number of transmission antennas, or the number of reception antennas) adjusted by performing the above-described operations to the second antenna combination, and may save current consumption for receiving the radar signal through the adjusted second antenna combination.

In an embodiment, when the distance to the measurement target (e.g., person) is short (e.g., less than a designated threshold) based on the radar signal and the biometric signal corresponding to any one (e.g., the third antenna combination) of the at least one antenna combination of operation 510, the electronic device 101 (e.g., the processor 120) may perform at least one of the following example, non-limiting, operations:

Reduce the number of transmission pulses for the third antenna combination by a designated value (or to a designated value); or Reduce the measurement distance for the third antenna combination by a designated value (or to a designated value).

In an embodiment, to adjust the measurement distance for the third antenna combination according to the distance to the measurement target measured based on the radar signal and the biometric signal, the electronic device 101 (e.g., the processor 120) may control the antennas of the third antenna combination to transmit signals and receive radar signals within the range of the distance. In an embodiment, the electronic device 101 (e.g., the processor 120) may generate a preprocessing matrix including a designated number of range bins by preprocessing a radar signal (e.g., sampled data), and may obtain a biometric signal based on the preprocessing matrix. The number of range bins may correspond to the measurement distance. For example, when one range bin corresponds to a measurement distance of 10 cm and the distance to the measurement target is 1.5 m, the electronic device 101 (e.g., the processor 120) may increase the SNR of the radar signal and decrease the storage capacity of the buffer for storing the sampled data by adjusting the number of range bins to 15.

In operation 535, the electronic device 101 (e.g., the processor 120) may track the movement of the measurement target (e.g., at least one person) based on the at least one radar signal and/or the biometric signal, thereby determining whether the distance to the measurement target and/or the posture of the measurement target is changed. In an embodiment, the electronic device 101 (e.g., the processor 120) may measure the distance to the measurement target and/or the posture every designated period, and when a variation in at least one of the distance and/or posture measured in the current period from the measurement value in the previous period is greater than, e.g., a designated value, determine that the distance to the measurement target and/or posture is changed and proceed to operation 505.

In operation 540, the electronic device 101 (e.g., the processor 120) may determine whether the signal quality of the at least one radar signal and/or biometric signal is changed. In an embodiment, the electronic device 101 (e.g., the processor 120) may measure the signal quality every designated period and, when the variation from at least one previous period is larger than, e.g., a designated value, determine that the signal quality is changed and proceed to operation 505.

When it is determined that the distance to the measurement target and the posture are not changed in operation 535, and/or when it is determined that the signal quality is not changed in operation 540, the electronic device 101 (e.g., the processor 120) may proceed to operation 515 to obtain a radar signal again from each antenna combination (e.g., at least one antenna combination selected in operation 530) to which the control parameters determined in operation 530 are applied. The electronic device 101 (e.g., the processor 120) may instruct the UWB communication circuit 200 to apply the control parameters to the selected at least one antenna combination.

FIG. 6A is a diagram illustrating various example mounting types of an electronic device 101 according to various embodiments.

Referring to FIG. 6A, the electronic device 101 may identify that the current mounting type of the UWB communication circuit 200 (e.g., the electronic device 101 including the UWB communication circuit 200) is any one of the mounting types 602, 604, 606, 608, 610, and 612. The first mounting type 602 may be a state in which the front surface (e.g., display screen) of the electronic device 101 faces away from the measurement target 600 on the tripod (on-tripod and back-side-object). The second mounting type 604 may be a state in which the front surface of the electronic device 101 faces the measurement target 600 on the tripod (on-tripod and screen-side-object). The third mounting type 606 may be a state in which the front surface of the electronic device 101 faces away from the ceiling on the table (side-table and back-side-ceiling). The fourth mounting type 608 may be a state in which the front surface of the electronic device 101 faces the ceiling on the table (side-table and screen-side-ceiling). The fifth mounting type 610 is a state in which the front surface of the electronic device 101 faces away from the measurement target 600 on a charger (charge-standing and back-side-object). The sixth mounting type 612 is a state in which the front surface of the electronic device 101 faces the measurement target 600 on the charger (charge-standing and screen-side-object).

In an embodiment, the electronic device 101 (e.g., the processor 120) may determine any one of the mounting types 602, 604, 606, 608, 610, and 612 based on sensor data collected from the acceleration sensor, the gyro sensor, and/or the proximity sensor included in the sensor module 176 and sensor data collected from the camera module 180.

Figure 6B:
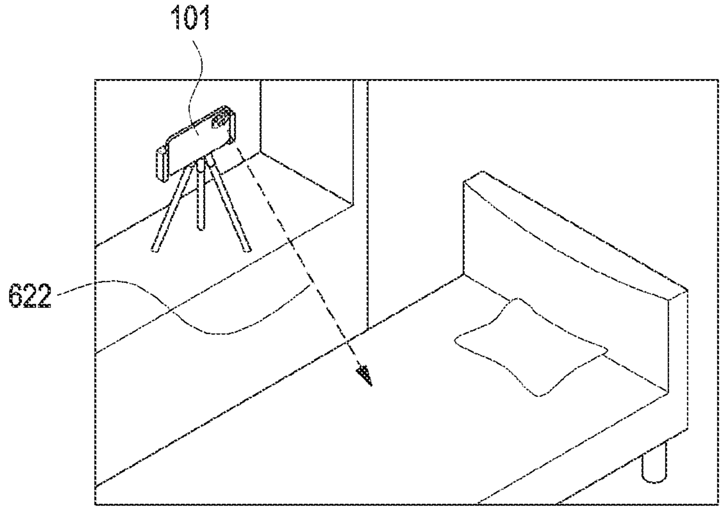
FIG. 6B is a diagram illustrating example mounting angles of an electronic device according to various embodiments.

FIG. 6B is a diagram illustrating example mounting angles of an electronic device 101 according to various embodiments.

Referring to FIG. 6B, the electronic device 101 may identify the mounting angle (e.g., the first mounting angle 622 or the second mounting angle 624) at which the electronic device 101 (e.g., the antennas 230 and 240 of the UWB communication circuit 200) faces the measurement target, based on sensor data collected from the acceleration sensor, the gyro sensor, and/or the proximity sensor included in the sensor module 176 and sensor data collected from the camera module 180. In an embodiment, the first mounting angle 622 when the electronic device 101 is disposed on the shelf may be larger than the second mounting angle 624 when the electronic device 101 is disposed on the tripod.

Figure 7A:
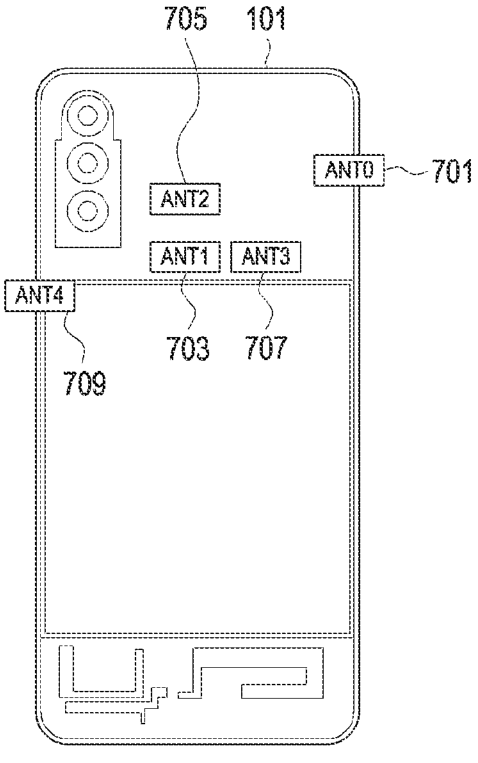
FIG. 7A is a diagram illustrating an arrangement of antennas for UWB communication according to various embodiments.

FIG. 7A is a diagram illustrating an arrangement of antennas for UWB communication according to various embodiments.

Referring to FIG. 7A, the electronic device 101 may include a plurality of antennas, e.g., ANT0 701, ANT1 703, ANT2 705, ANT3 707, and ANT4 709, which may be used for UWB communication. In an embodiment, the ANT0 701 and the ANT4 709 may be disposed close to a side surface of the housing (e.g., the housing 300) of the electronic device 101, and may be implemented as a metal antenna. For example, the ANT0 701 and the ANT4 709 may correspond to at least one distance ranging antenna 230 of FIG. 3. In an embodiment, the ANT1 703, the ANT2 705, and the ANT3 707 may be disposed at positions far from the side surface of the housing (e.g., the housing 300) of the electronic device 101 and close to the rear surface, and may be implemented as patch antennas. For example, the ANT1 703, ANT2 705, and ANT3 707 may correspond to one or more AoA ranging antennas 240 of FIG. 3. In an embodiment, at least one of the ANT0 701, the ANT1 703, the ANT2 705, the ANT3 707, and the ANT4 709 may be a bidirectional antenna and may operate as a transmission antenna or a reception antenna under the control of the electronic device 101 (e.g., the processor 120).

Figure 7B:
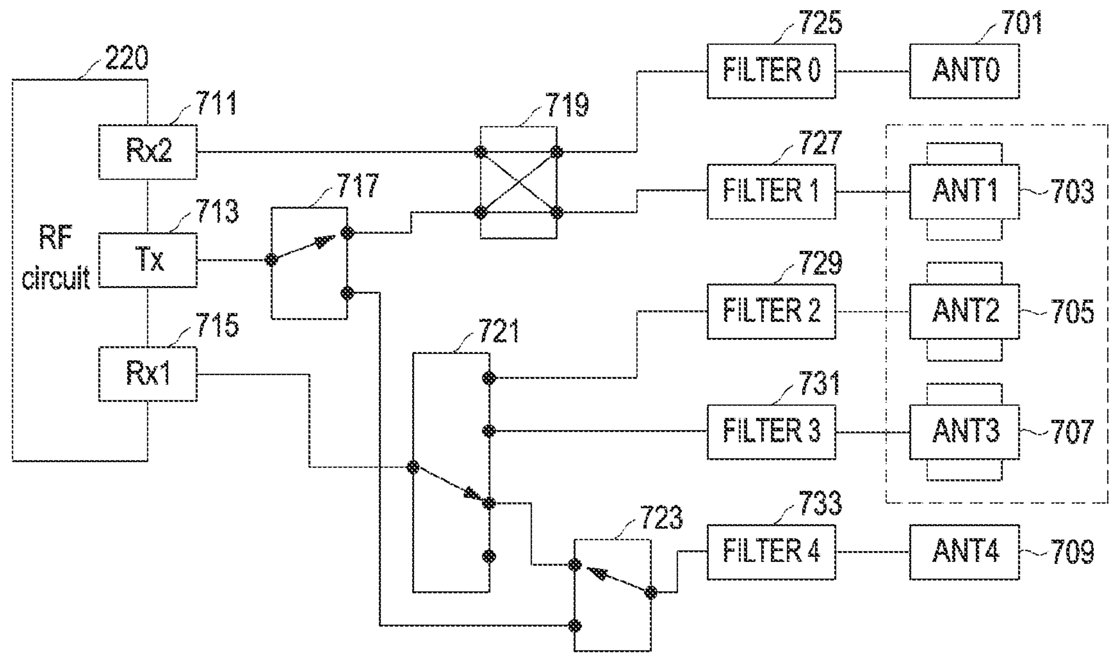
FIG. 7B is a diagram illustrating connection of antennas for UWB communication according to various embodiments.

FIG. 7B is a diagram illustrating connection of antennas for UWB communication according to various embodiments.

Referring to FIG. 7B, the RF circuit 220 may be coupled to the ANT0 701, the ANT1 703, the ANT2 705, the ANT3 707, and the ANT4 709 through one output (e.g., the first transmission port Tx 713) and two inputs (e.g., the first reception port Rx1 715 and the second reception port Rx2 711). The transmission signal (e.g., a signature signal) output from the first transmission port 713 may be transferred to the second switch 719 (e.g., a double pole double through (DPDT)) or the fourth switch 723 (e.g., SPDT)) through the first switch 717 (e.g., a single pole double throw (SPDT)). The second switch 719 may transfer the transmission signal to the ANT0 701 through the filter 0 725 (e.g., BPF) or may transfer the transmission signal to the ANT1 703 through the filter 1 727 (e.g., BPF). The fourth switch 723 may transfer the transmission signal to the ANT4 709 through the filter 4 733 (e.g., BPF).

The first reception signal detected by the ANT0 701 may be input to the second reception port 711 by the second switch 719 via the filter 0 725. The second reception signal detected by the ANT1 703 may be input to the second reception port 711 by the second switch 719 via the filter 1 727 (e.g., BPF). The third reception signal detected by the ANT2 705 may be input to the first reception port 715 by the third switch 721 (e.g., single pole four throw (SP4T)) via the filter 2 729 (e.g., BPF). The fourth reception signal detected by the ANT3 707 may be input to the first reception port 715 by the third switch 721 (e.g., single Pole four throw (SP4T)) via the filter 3 731 (e.g., BPF). The fifth reception signal detected by the ANT4 709 may be transferred to the third switch 721 by the fourth switch 723 via the filter 5, 733, and the third switch 721 may input the fifth reception signal to the first reception port 715.

The electronic device 101 may select at least one transmission antenna (e.g., at least one of ANT0 701, ANT1 703, or ANT4 709) to be included in the antenna combination by controlling the first to fifth switches 717, 719, 721, and 723. The electronic device 101 (e.g., the processor 120) may select at least one reception antenna (e.g., at least one of ANT0 701, ANT1 703, ANT2 705, ANT3 707, or ANT4 709) to be included in the antenna combination by controlling the first to fifth switches 717, 719, 721, and 723.

The electronic device 101 may control the first to fifth switches 717, 719, 721, and 723 such that at least one transmission antenna corresponding to the number of transmission antennas designated according to the control parameters is connected to the transmission port 713. The electronic device 101 may control the first to fifth switches 717, 719, 721, and 723 such that at least one reception antenna corresponding to the number of reception antennas designated according to the control parameters is connected to the first reception port 715 and the second reception port 711.

According to an embodiment, in operation 510 above, the electronic device 101 may control the first to fifth switches 717, 719, 721, and 723 to be connected to antennas appropriate for collecting radar signals from the measurement target according to the number of transmission antennas and the number of reception antennas designated according to control parameters determined by default. According to an embodiment, in operation 510, the electronic device 101 may control the first to fifth switches 717, 719, 721, and 723 to be connected to antennas suitable for collecting radar signals from the measurement target according to the number of transmission antennas and the number of reception antennas determined according to the signal quality of the radar signal and/or biometric signal in operation 530.

Figure 8A:
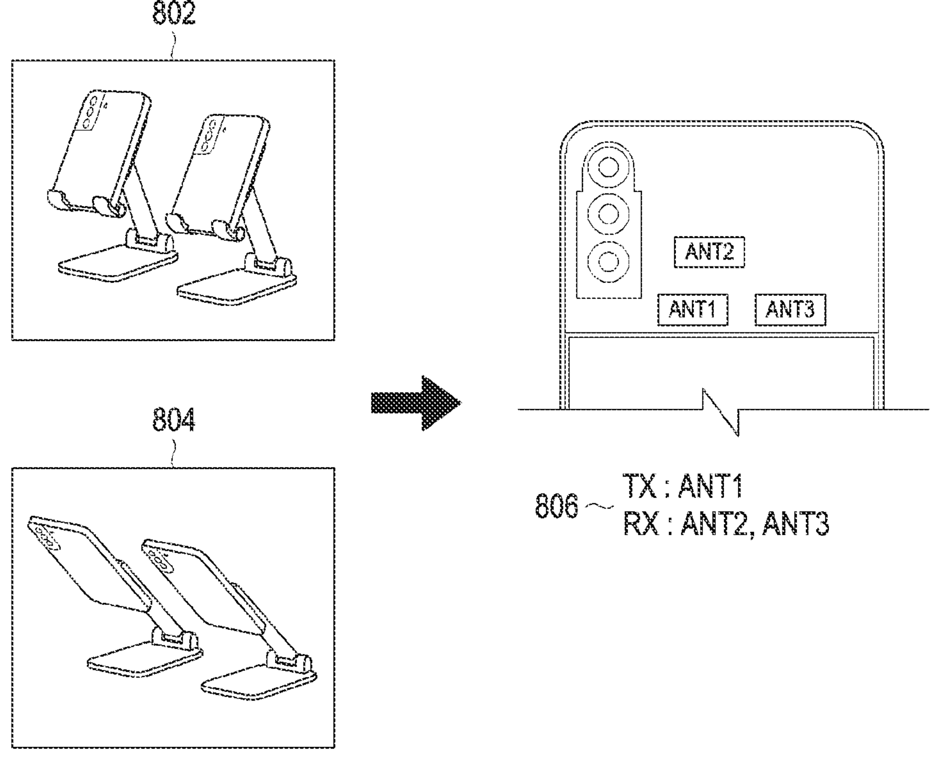
FIGS. 8A and 8B are diagrams illustrating selection of an antenna combination according to a mounting state according to various embodiments.
Figure 8B:
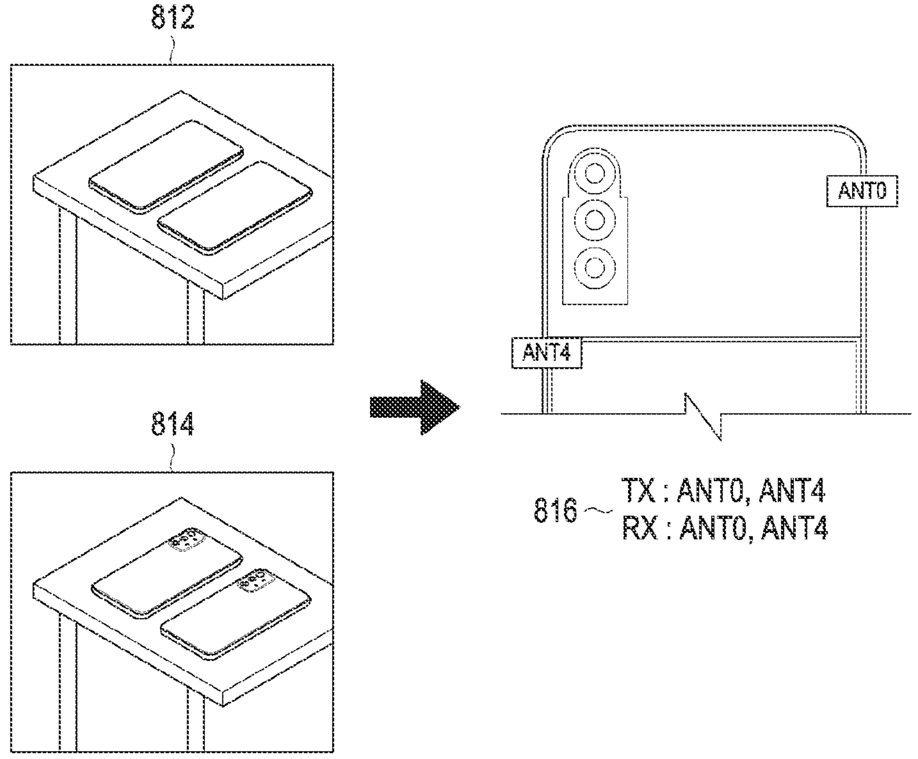

FIGS. 8A and 8B are diagram illustrating example selection of an antenna combination according to a mounting state according to various embodiments.

Referring to FIG. 8A, when the mounting type of the electronic device 101 is an on-tripod and back-side-object state 802 or a charger-standing and back-side-object state 804, the electronic device 101 may select an antenna combination 806 including the ANT1 703 as a transmission antenna and including the ANT2 705 and/or ANT3 707 as a reception antenna. For example, the electronic device 101 may enhance the reception quality of the radar signal by selecting the antenna combination 806 including the ANT1 703, the ANT2 705, and the ANT3 707 disposed on the rear surface of the housing of the electronic device 101.

Referring to FIG. 8B, when the mounting type of the electronic device 101 is a side-table and screen-side-ceiling state 812 or a side-table and back-side-ceiling state 814, the electronic device 101 may select an antenna combination 816 including ANT0 701 and/or ANT4 709 as a transmission antenna and ANT0 701 and/or ANT4 709 as a reception antenna.

For example, the electronic device 101 may enhance the reception quality of the radar signal by selecting the antenna combination 816 including the ANT0 701 and the ANT4 709 disposed on the side surface of the housing of the electronic device 101.

Figure 9:
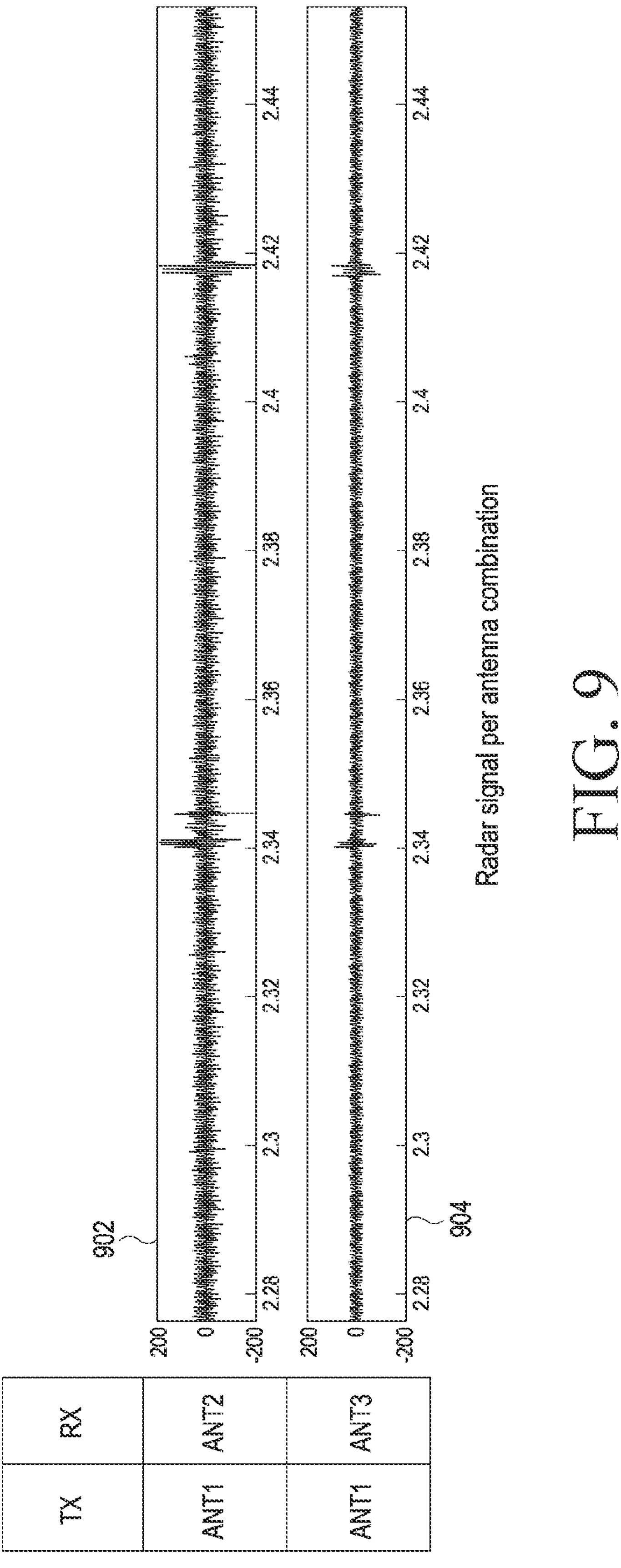
FIG. 9 is a graph illustrating a radar signal per antenna combination according to various embodiments.

FIG. 9 is a diagram including graphs illustrating a radar signal per antenna combination according to various embodiments.

Referring to FIG. 9, the first radar signal 902 is received through the first antenna combination including ANT1 703 and ANT2 705, and the second radar signal 904 is received through the second antenna combination including ANT1 703 and ANT3 707. In an embodiment, the electronic device 101 may identify that the signal quality (e.g., SNR) of the first radar signal 902 is better than that of the second radar signal 904, and may select the first antenna combination corresponding to the first radar signal 902 or may not select the second antenna combination corresponding to the second radar signal 904 in operation 530.

Figure 10A:
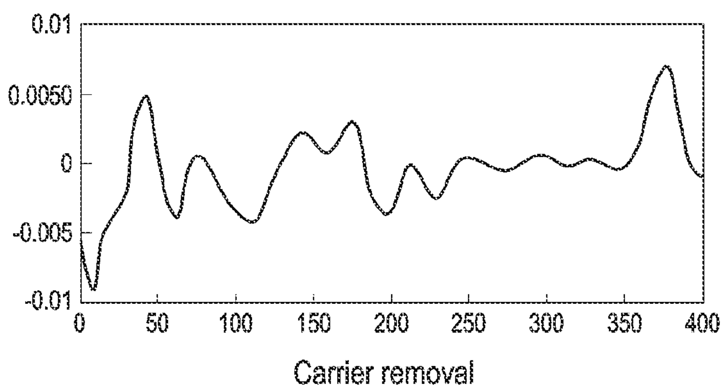
FIGS. 10A and 10B are graphs illustrating signal processing of a radar signal according to various embodiments.
Figure 10A:
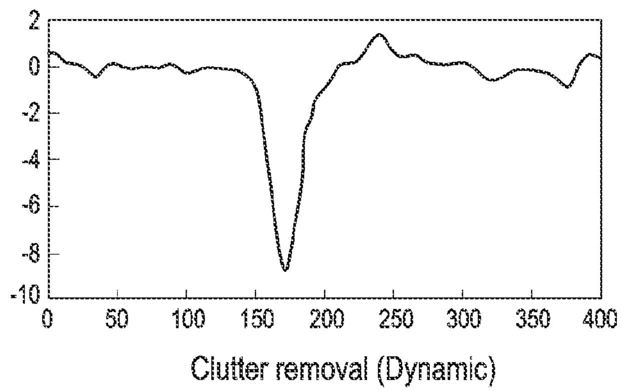
Figure 10A:
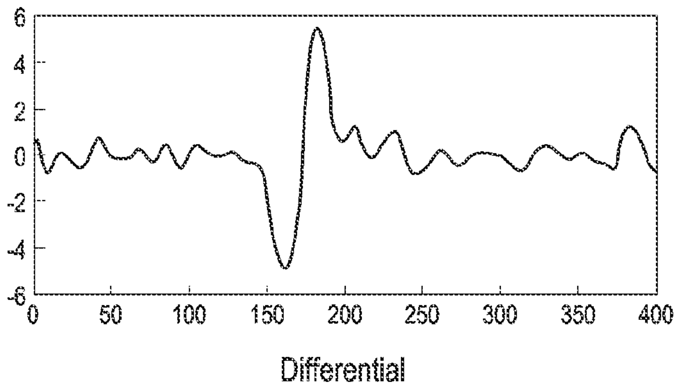
Figure 10B:
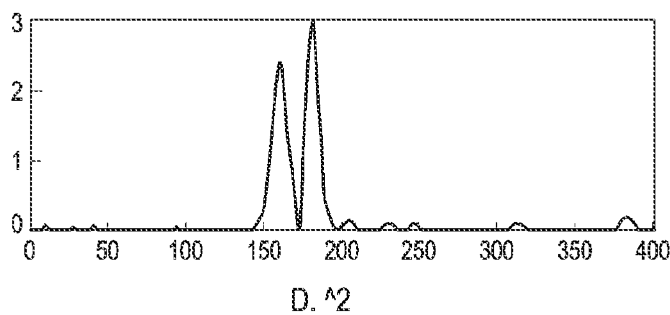
Figure 10B:
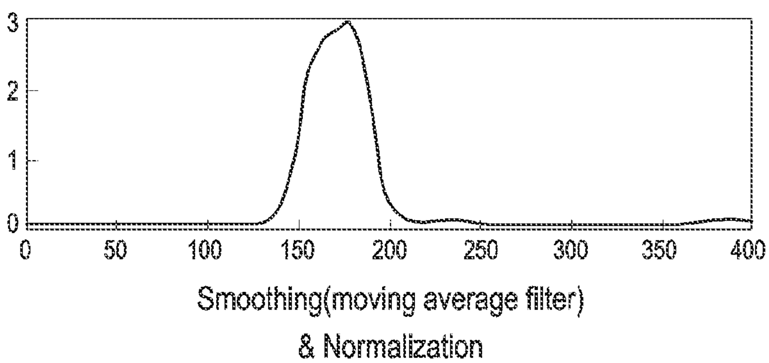
Figure 10B:
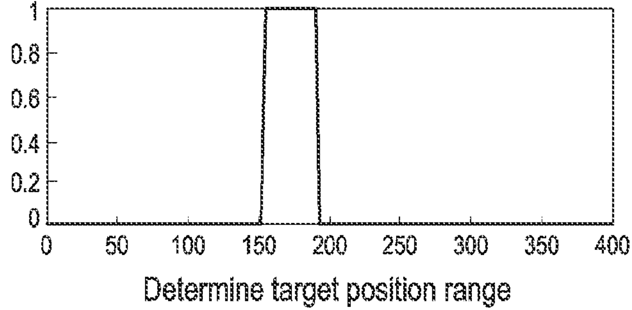

FIGS. 10A and 10B are graphs illustrating signal processing of a radar signal according to various embodiments.

Referring to FIG. 10A, the electronic device 101 may perform preprocessing 1002 on radar signals (e.g., the first radar signal 902 and the second radar signal 904). The preprocessing 1002 may include carrier removal, clutter removal, and differential demodulation.

Referring to FIG. 10B, the electronic device 101 may determine the distance (e.g., the position range) 1004 of the measurement target using the signal that has undergone preprocessing 1002.

Figure 11:
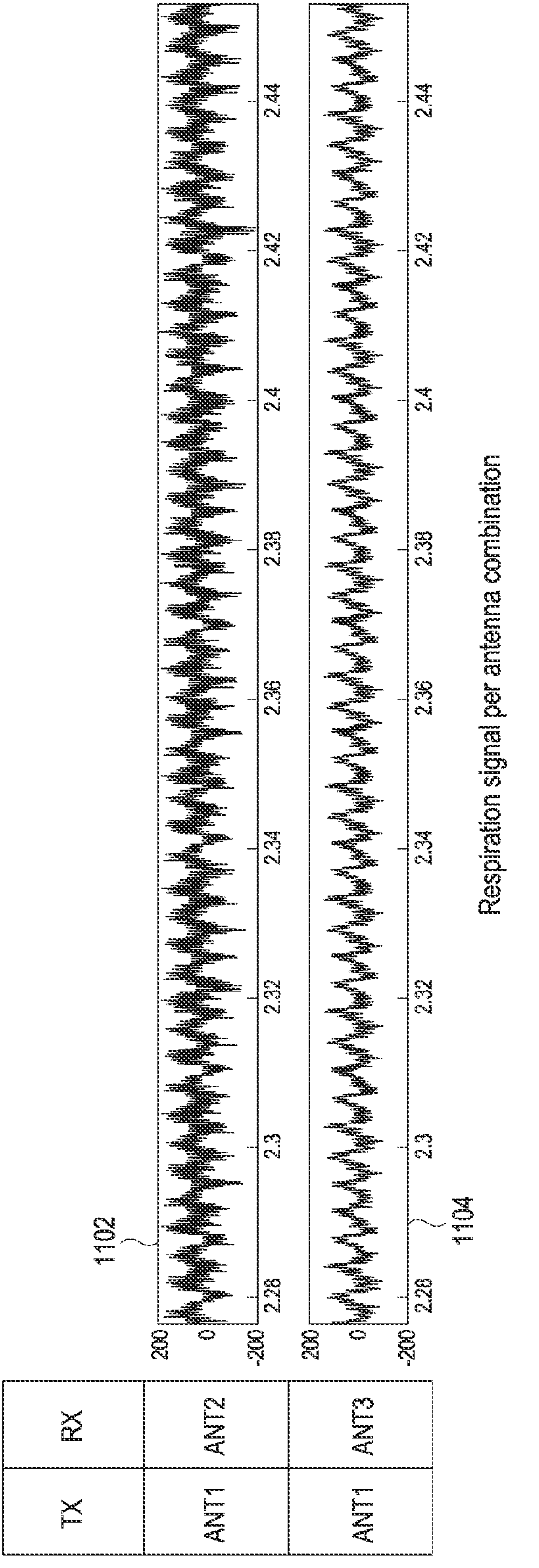
FIG. 11 is a graph illustrating extraction of a biometric signal according to various embodiments.

FIG. 11 is a diagram including graphs illustrating extraction of a biometric signal according to various embodiments.

Referring to FIG. 11, the electronic device 101 may extract the first biometric signal 1102 (e.g., the respiration signal and/or the heart rate signal) from the first radar signal 902 received through the first antenna combination including ANT1 703 and ANT2 705 through preprocessing 1002. The electronic device 101 may extract a second biometric signal 1104 (e.g., a respiration signal and/or a heart rate signal) from the first radar signal 904 received through the second antenna combination including ANT1 703 and ANT3 707 through the preprocessing 1002. In an embodiment, the electronic device 101 may identify that the signal quality (e.g., SNR) of the first biometric signal 1102 is better than that of the second biometric signal 1104, and may select a first antenna combination corresponding to the first biometric signal 1102 or may not select a second antenna combination corresponding to the second biometric signal 1104 in operation 530.

FIGS. 12A, 12B, 12C, 12D, 12E, and 12F are diagrams and graphs illustrating an example operation of determining the distance and/or posture of a measurement target according to various embodiments.

Figure 12A:
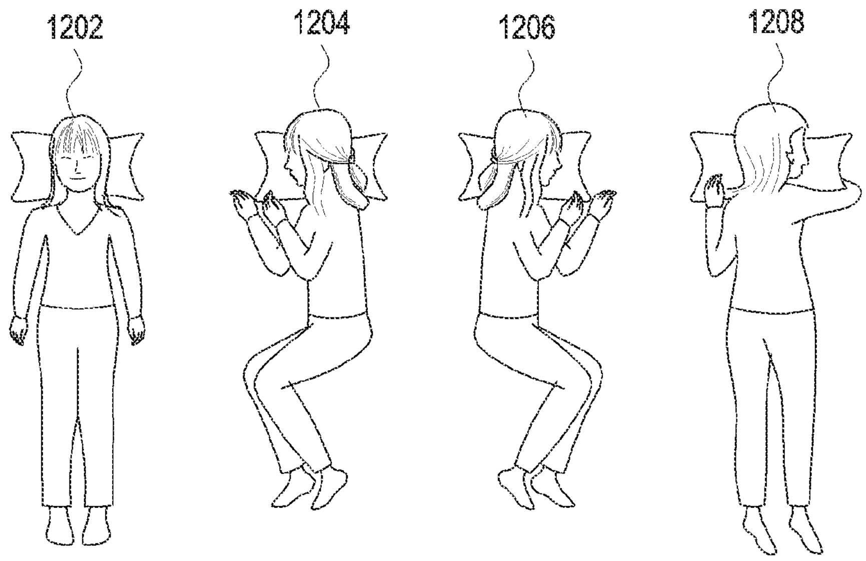
FIGS. 12A, 12B, 12C, 12D, 12E, and 12F are diagrams illustrating an example operation of determining the distance and/or posture of a measurement target according to various embodiments.

Referring to FIG. 12A, the electronic device 101 may determine that the measurement target (e.g., a person) is in a sleep state based on a biometric signal (e.g., a respiration signal) extracted from a radar signal (e.g., the first radar signal 902 or the second radar signal 904), and that the current posture of the measurement target is any one of a supine posture 1202, a lateral right posture 1204, a lateral left posture 1206, or a prone posture 1208.

Figure 12B:
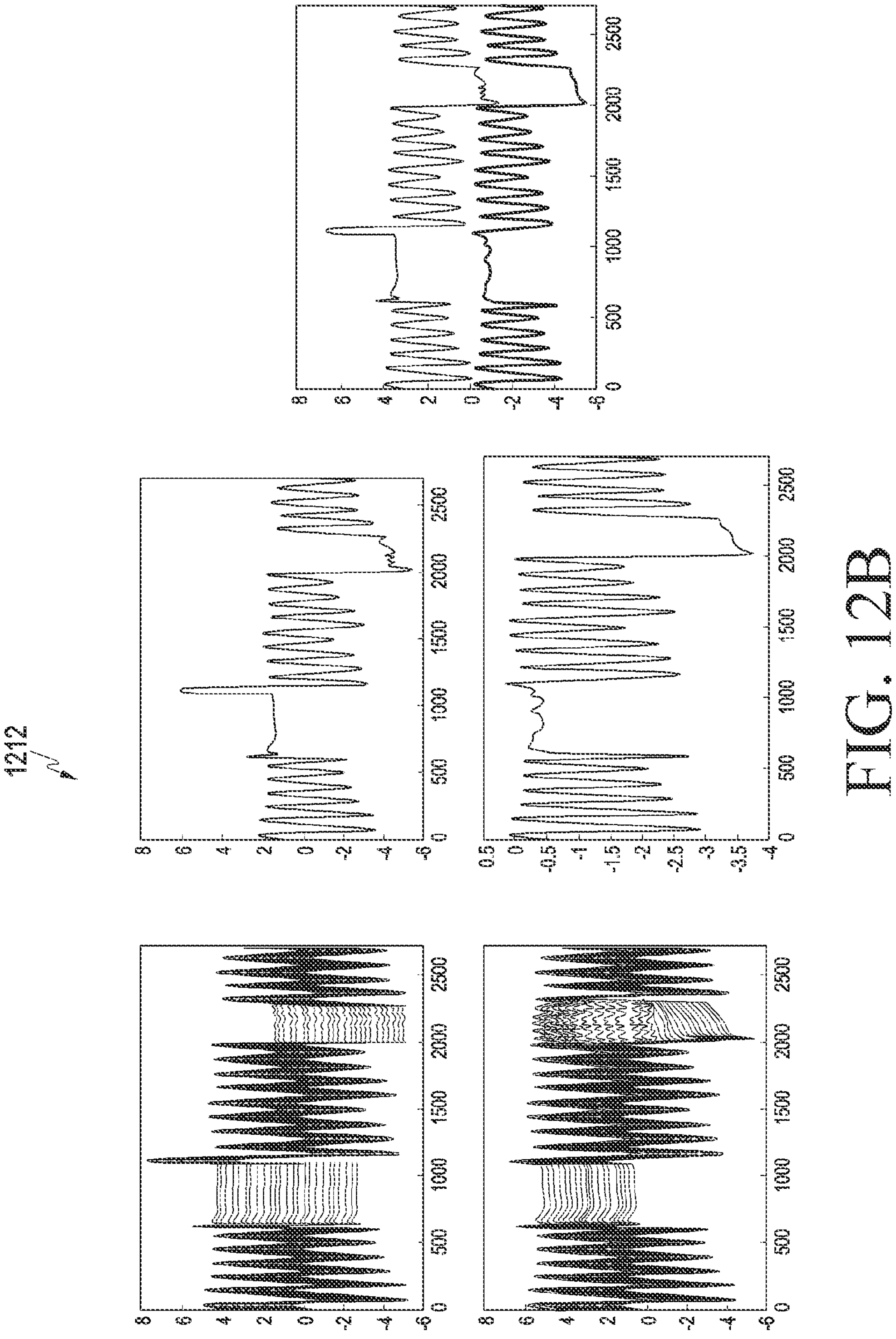

Referring to FIG. 12B, the electronic device 101 may determine that the measurement target is in the supine posture 1202, based on the respiration signal having a designated first signal pattern 1212 corresponding to the supine posture 1202.

Figure 12C:
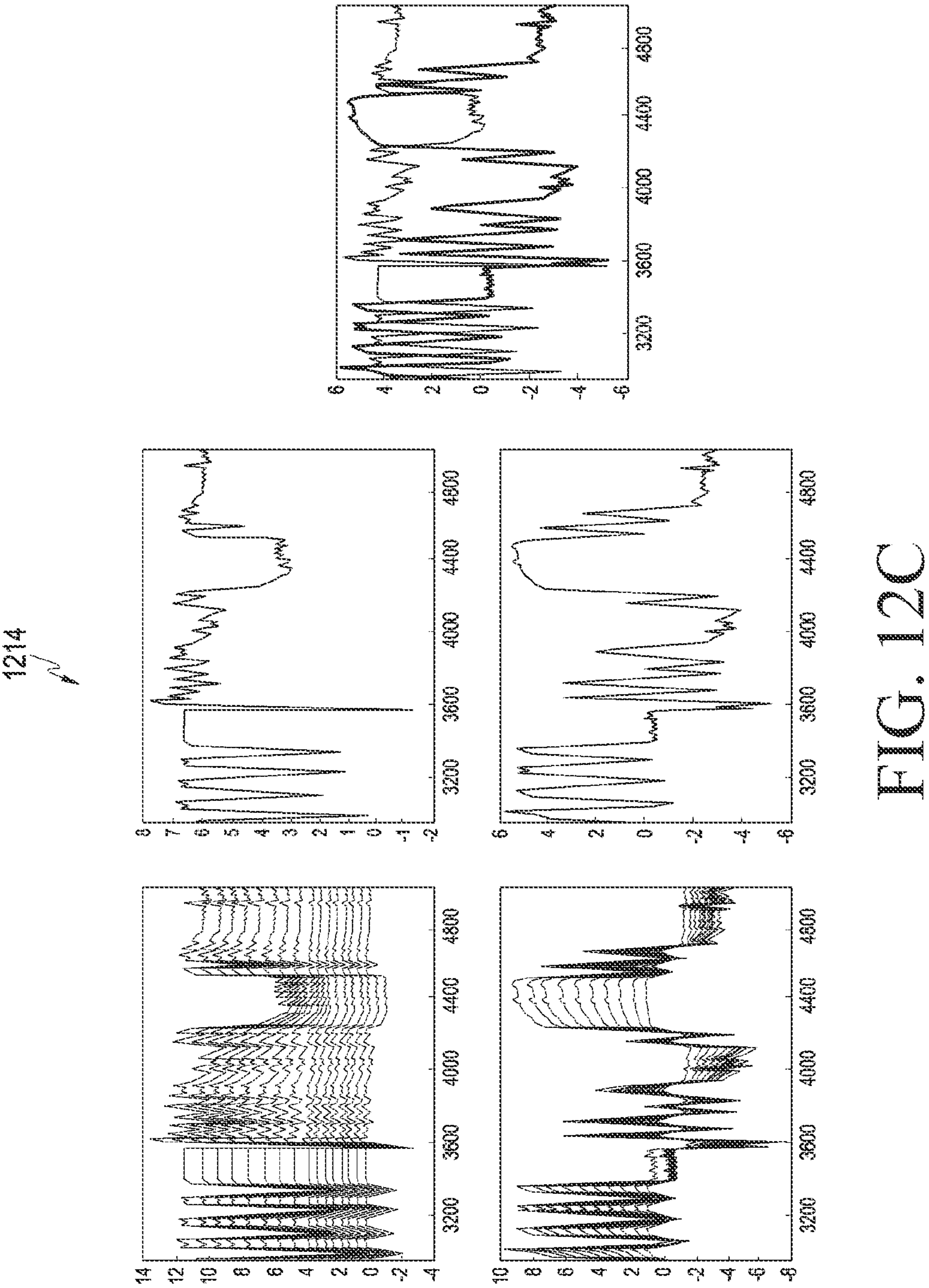

Referring to FIG. 12C, the electronic device 101 may determine that the measurement target is in the lateral right posture 1204, based on the respiration signal having a designated second signal pattern 1214 corresponding to the lateral right posture 1204.

Figure 12D:
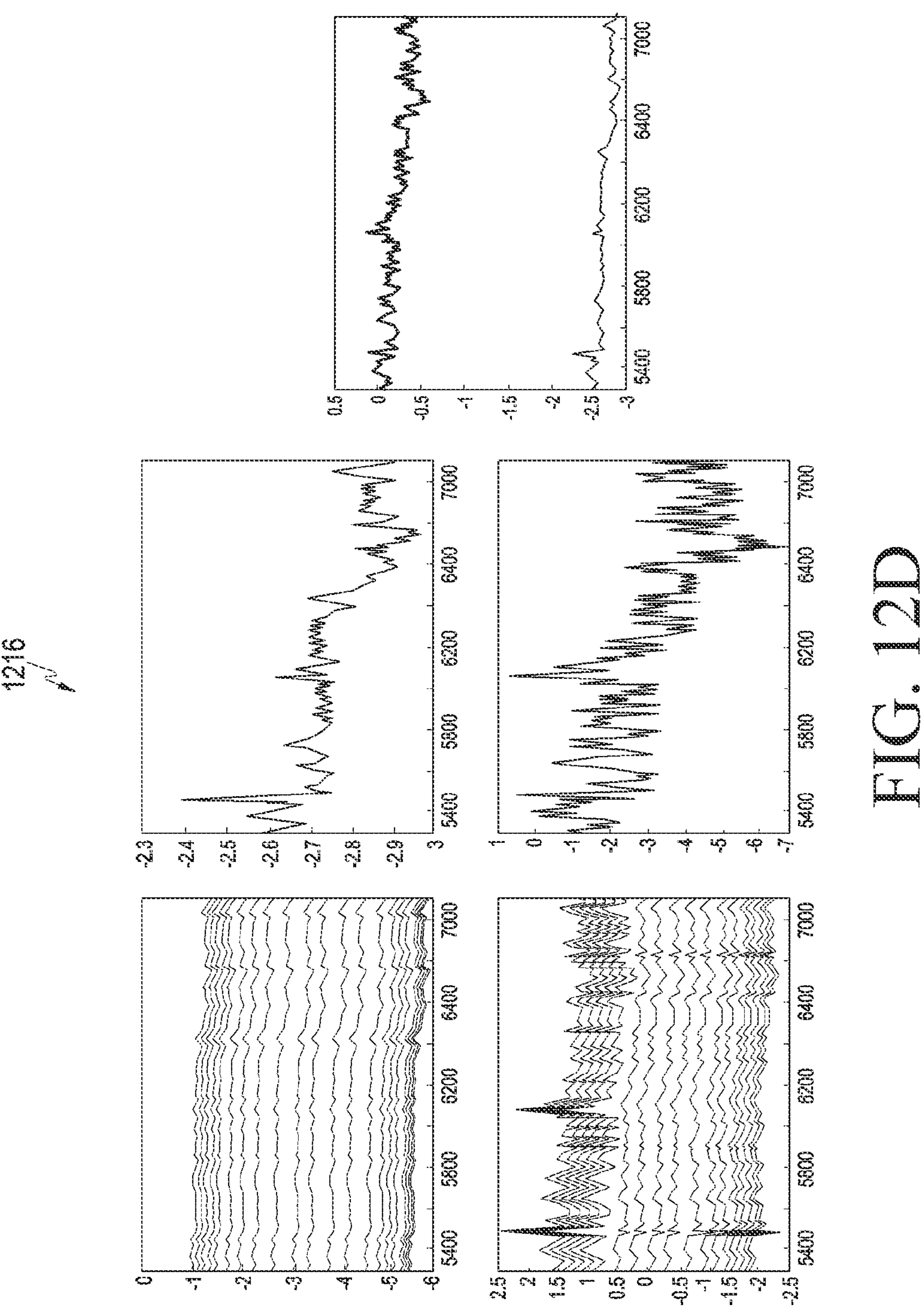

Referring to FIG. 12D, the electronic device 101 may determine that the measurement target is in the lateral left posture 1206, based on the respiration signal having a designated third signal pattern 1216 corresponding to the lateral left posture 1206.

Figure 12E:
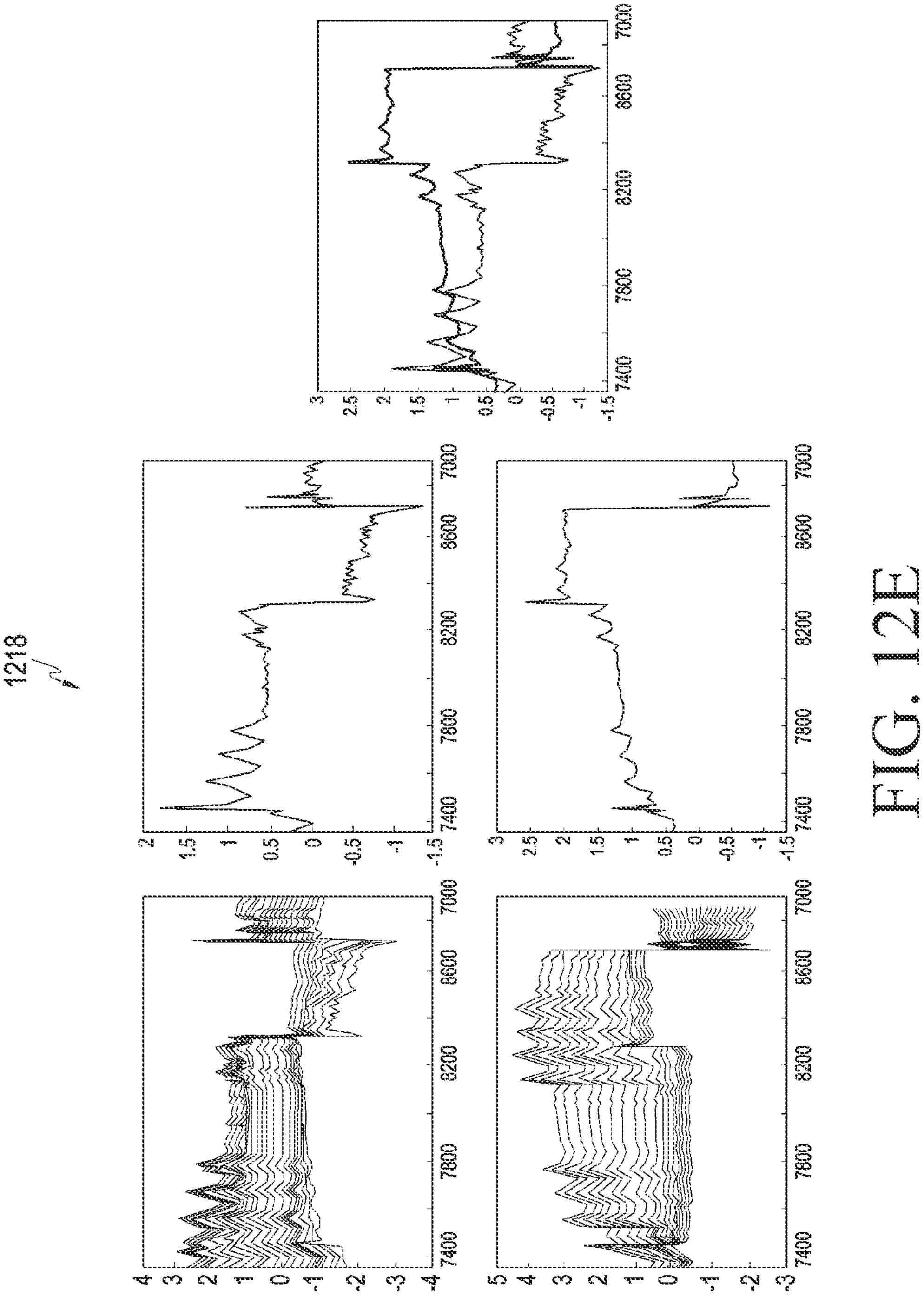

Referring to FIG. 12E, the electronic device 101 may determine that the measurement target is in the prone posture 1208, based on the respiration signal having a designated fourth signal pattern 1218 corresponding to the prone posture 1208.

Figure 12F:
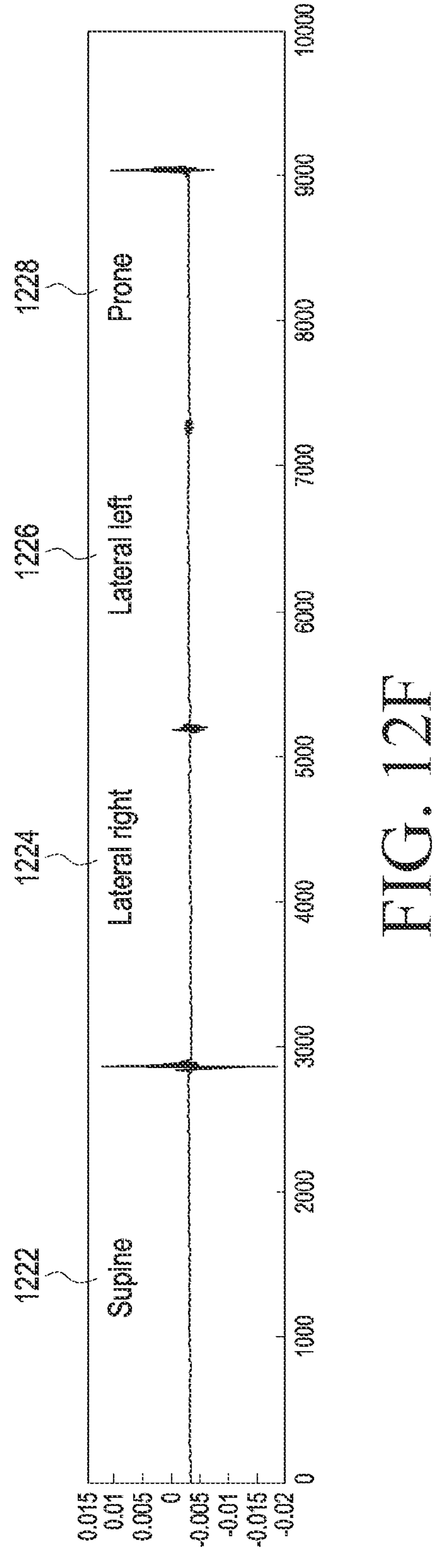

Referring to FIG. 12F, the electronic device 101 may track the posture of the measurement object to identify that the posture of the measurement object is changed in the order of, e.g., the supine posture 1222, the lateral right posture 1224, the lateral left posture 1226, and the prone posture 1228.

Figure 13A:
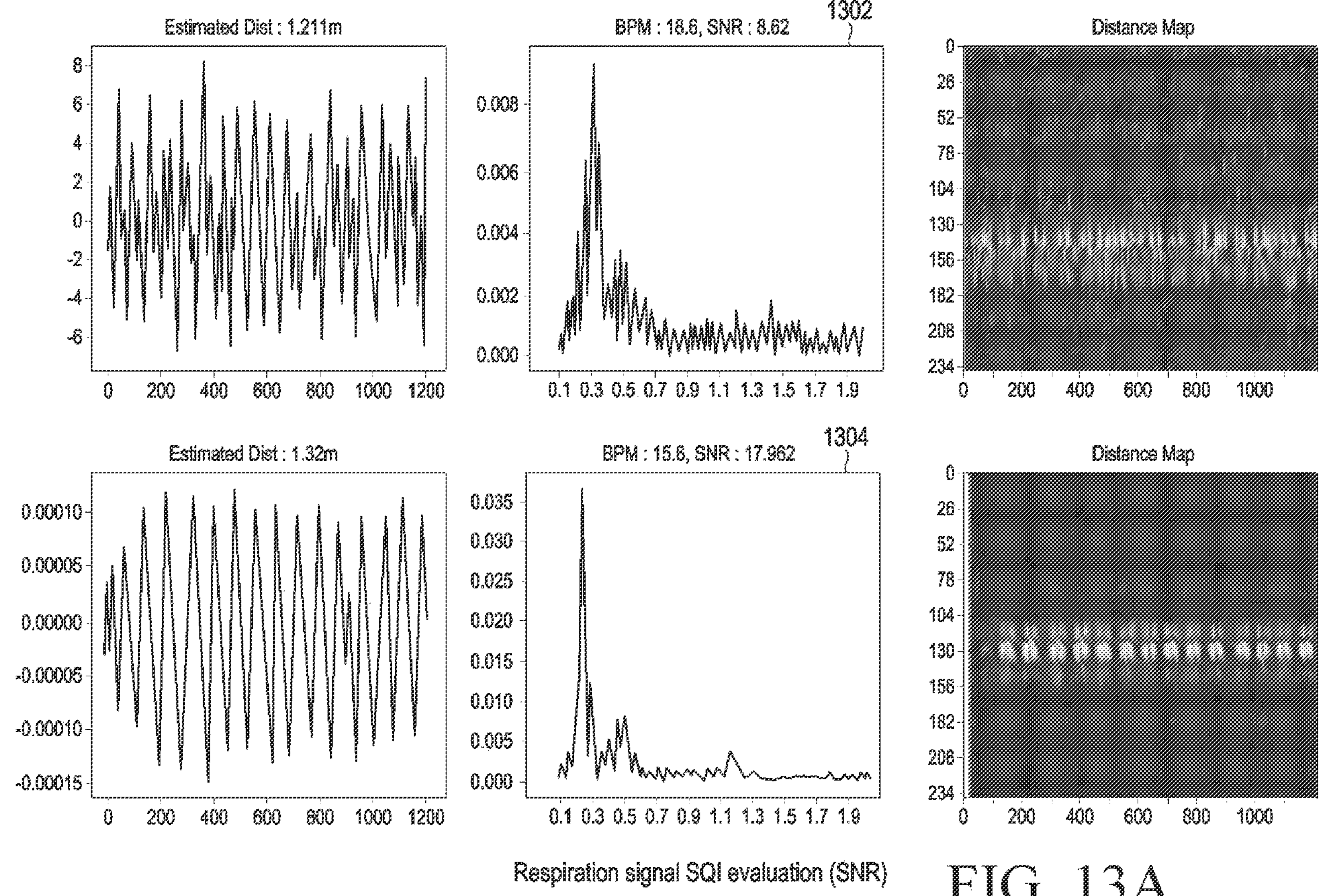
FIGS. 13A and 13B are graphs illustrating signal quality evaluation of a respiration signal according to various embodiments.
Figure 13B:
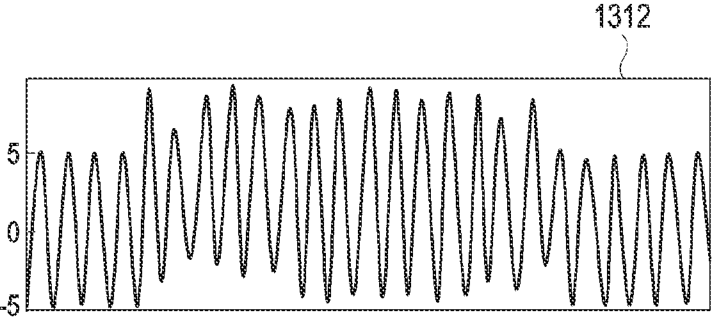
Figure 13B:
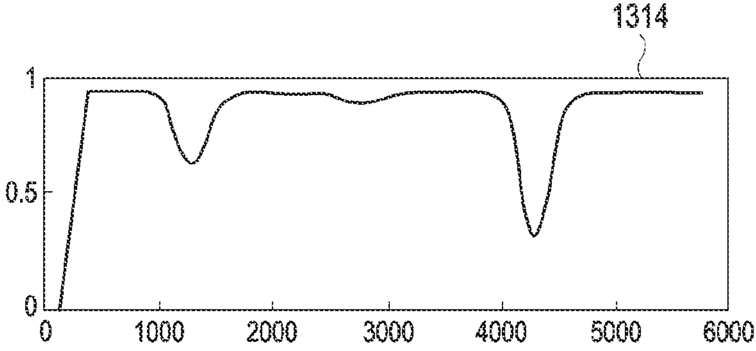

FIGS. 13A and 13B are graphs illustrating signal quality evaluation of a respiration signal according to various embodiments.

Referring to FIG. 13A, the electronic device 101 may calculate an estimated distance to the measurement target, breaths per minute (BPM), and a signal-to-noise ratio (SNR) based on the radar signal and the respiration signal related thereto. For example, when the first SNR 1302 of the respiration signal corresponding to the first radar signal is 8.62 and the second SNR 1304 of the respiration signal corresponding to the second radar signal is 17.962, the electronic device 101 may select an antenna combination corresponding to the second radar signal and/or may not select an antenna combination corresponding to the first radar signal.

Referring to FIG. 13B, the electronic device 101 may calculate an autocorrelation value 1314 based on the respiration signal 1312 extracted from the radar signal. For example, the autocorrelation value 1314 may be calculated by correlating a signal component of a current time interval (e.g., a signal in a designated time window) of the respiration signal 1312 with a signal component of a past time interval. The autocorrelation value 1314 may be within a range of 0.0 to 1.0, and the electronic device 101 may determine that as the autocorrelation value 1314 gets closer to 1, the signal quality enhances.

Figure 14A:
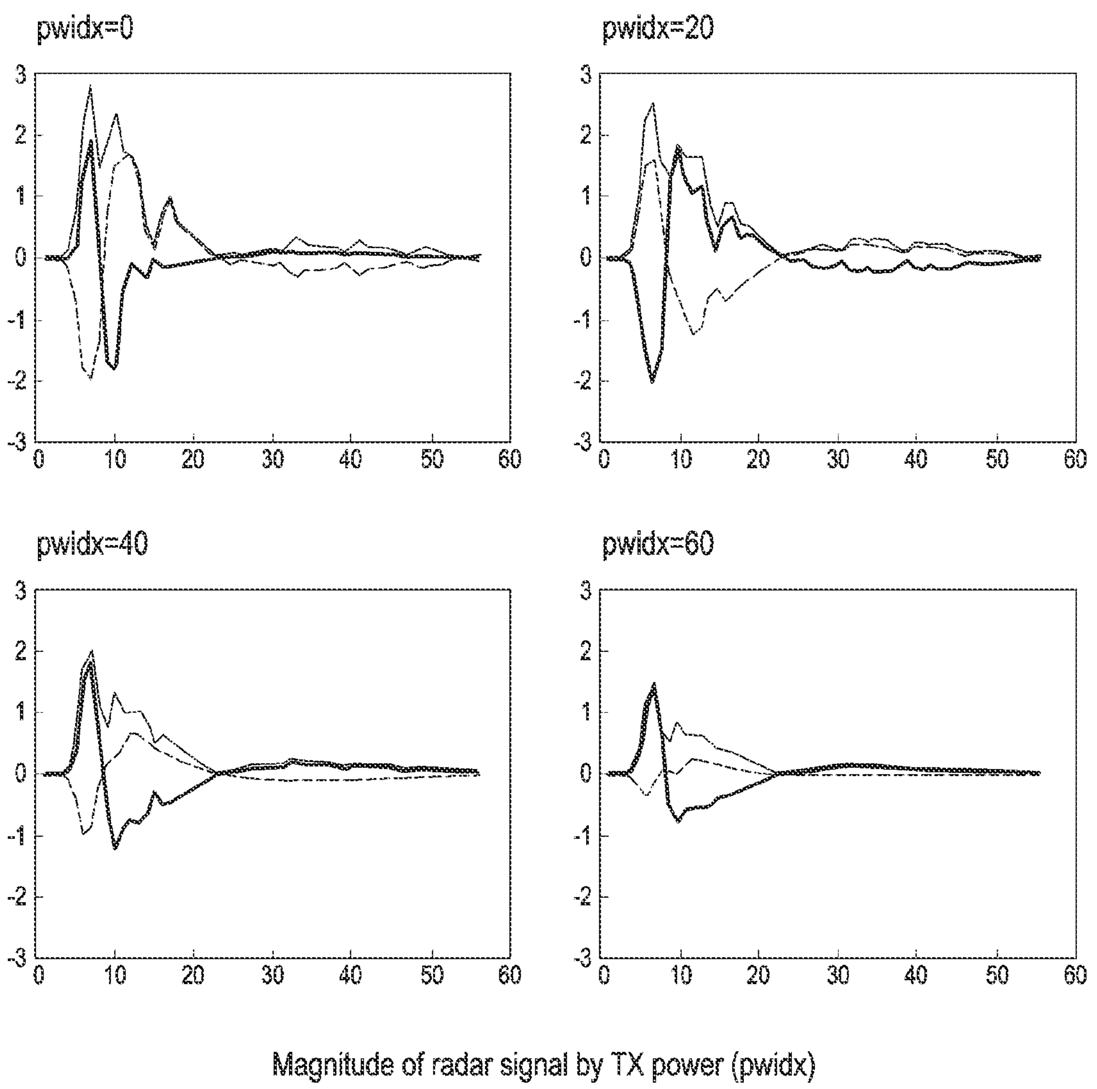
FIGS. 14A and 14B are graphs illustrating adjustment of control parameters according to various embodiments.
Figure 14B:
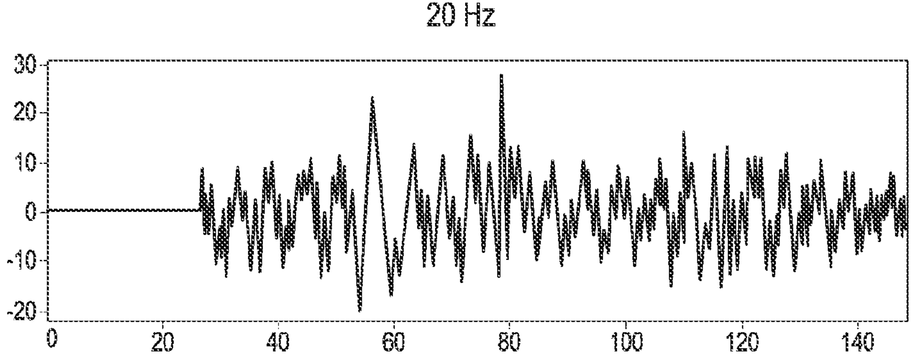
Figure 14B:
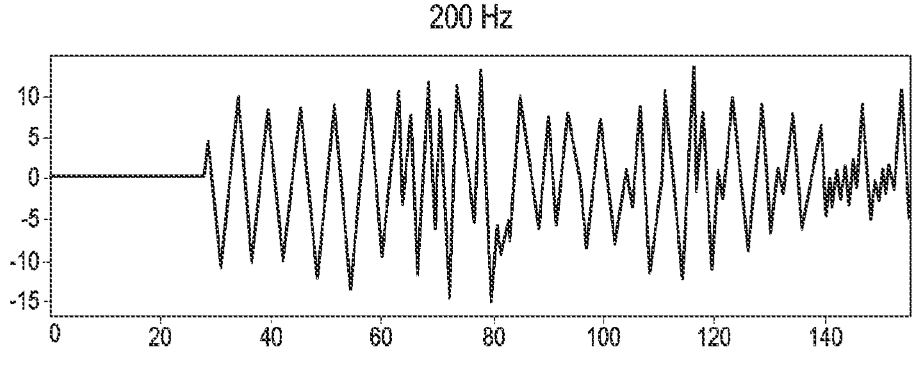

FIGS. 14A and 14B are graphs illustrating adjustment of control parameters according to various embodiments.

Referring to FIG. 14A, the amplitude 1410 of the radar signal may be changed according to the power index (pwidx) (e.g., pwidx=0, 20, 40, or 60) indicating transmission power of the signal (e.g., the signature signal) transmitted by the UWB communication circuit 200. The electronic device 101 may increase transmission power to enhance the signal quality of the radar signal corresponding to the selected antenna combination.

Referring to FIG. 14B, the waveform of the respiration signal 1420 may change according to the sampling rate (e.g., 20 Hz or 200 Hz) used by the UWB communication circuit 200 to sample the radar signal. The electronic device 101 may increase the sampling rate to enhance the signal quality of the biometric signal corresponding to the selected antenna combination.

Figure 15:
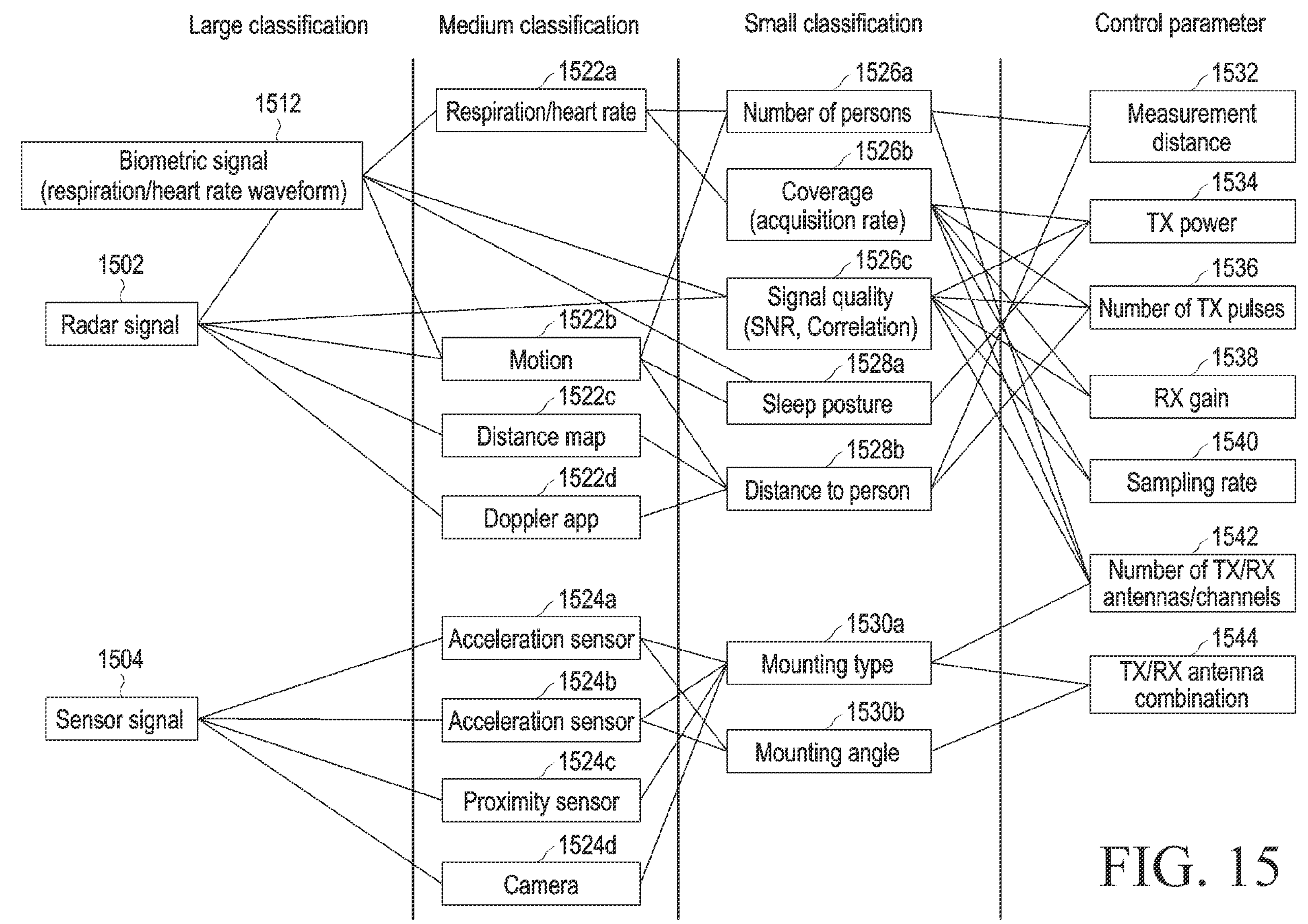
FIG. 15 is a diagram illustrating adjustable control parameters according to various embodiments.

FIG. 15 is a diagram illustrating adjustable control parameters according to various embodiments. According to various embodiments, the electronic device 101 may determine at least one of evaluation indicators and control parameters to be described in greater detail below.

Referring to FIG. 15, the control parameters may include at least one of the measurement distance 1532, transmission power 1534, the number of transmission pulses 1536, the reception gain 1538, the sampling rate 1540, the number of transmission/reception antennas 1542, or the antenna combination 1544. The control parameters may be adjusted based on evaluation indicators to be described below determined based on the radar signal 1502 and the sensor signal 1504.

The electronic device 101 may obtain a radar signal 1502 through the USB communication circuit 200 and may extract a biometric signal 1512 (e.g., a respiration signal and/or a heart rate signal) from the radar signal 1502. The electronic device 101 may obtain biometric data 1522*a* (e.g., a respiratory rate and/or a heart rate) of the measurement target from the biometric signal 1512. The electronic device 101 may obtain motion data 1522*b* of the measurement target based on the radar signal 1502 and the biometric signal 1512. The electronic device 101 may obtain a distance map 1522*c* and a Doppler map 1522*d* from the radar signal 1502.

In an embodiment, the electronic device 101 may determine the number of persons 1526*a* (e.g., the number of persons detected within the radar field of view) included in the measurement target and the coverage 1526*b*, based on the biometric data 1522*a* (e.g., the respiration signal). In an embodiment, the electronic device 101 may determine the signal quality 1526*c* (e.g., the SNR 1302 or 1304 or the autocorrelation value 1314) based on the radar signal 1502 and the biometric data 1522*a* (e.g., a respiration signal).

In an embodiment, the electronic device 101 may determine the sleep posture 1528*a* of each person included in the measurement target, based on the biometric signal 1512 and the motion data 1522*b*. In an embodiment, the electronic device 101 may determine the distance 1528*b* to each person included in the measurement target, based on the motion data 1522*a*, the distance map 1522*c*, and/or the Doppler map 1522*d*.

Figure 6B:
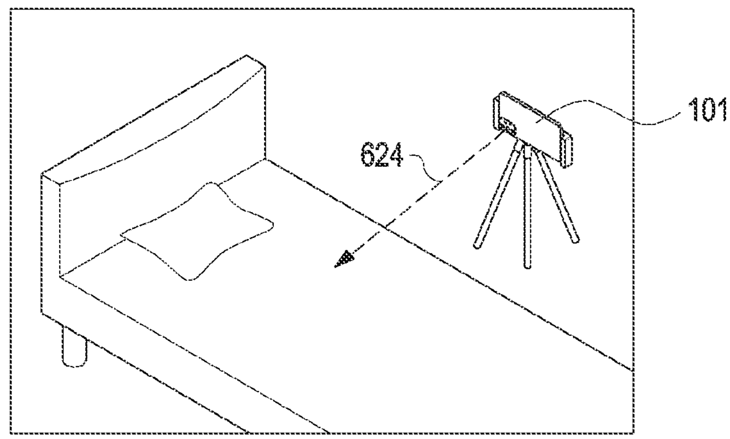

The electronic device 101 may obtain at least one sensor signal 1504, e.g., acceleration sensor data 1524*a*, gyro sensor data 1524*b*, proximity sensor data 1524*c*, or camera data 1524*d*, from the sensor module 176 and the camera module 180. In an embodiment, the electronic device 101 may determine the mounting type 1530*a* of the electronic device 101 based on at least one of the acceleration sensor data 1524*a*, the gyro sensor data 1524*b*, the proximity sensor data 1524*c*, or the camera data 1524*d*. In an embodiment, the mounting type 1530*a* may be any one of the mounting types 602, 604, 606, 608, 610, and 612 of FIG. 6. The electronic device 101 may determine the mounting angle 1530*b* of the electronic device 101 based on the acceleration sensor data 1524*a* and/or the gyro sensor data 1524*b*. The mounting angle 1530*b* may indicate the direction in which the electronic device 101 (e.g., the antennas 230 and 240 of the UWB communication circuit 200) faces the measurement target.

The electronic device 101 may adjust the measurement distance 1532 of the UWB communication circuit 200 based on the number of persons 1526*a* and/or the distance 1528*b* to each person. In an embodiment, when the distance to the measurement target (e.g., a person) is short (e.g., smaller than a designated threshold), the electronic device 101 may reduce the measurement distance 1532 by a designated value (or to a designated value).

The electronic device 101 may adjust the transmission power 1534 and/or the number of transmission pulses 1536 of the UWB communication circuit 200 based on at least one of the coverage 1526*b*, the signal quality 1526*c*, or the sleep posture 1528*a*. In an embodiment, when the signal acquisition rate indicated by the coverage 1526*b* is low (e.g., less than a designated threshold value), when the signal quality 1526*c* is low (e.g., less than a designated threshold value), and when the measurement target (e.g., a person) is detected as facing away from the electronic device 101 according to the sleep posture 1528*a*, the electronic device 101 may increase the transmission power 1534 and/or the number of transmission pulses 1536 by a designated value (or to a designated value). In an embodiment, when the signal acquisition rate indicated by the coverage 1526*b* is high (e.g., larger than the designated threshold), when the signal quality 1526*c* is high (e.g., larger than a designated threshold), and when the measurement target (e.g., a person) is detected as facing the electronic device 101 according to the sleep posture 1528*a*, the electronic device 101 may decrease the transmission power 1534 by a designated value (or to a designated value). In an embodiment, when the distance 1528*b* to the person included in the measurement object is close (e.g., less than a designated threshold), the electronic device 101 may reduce the number of transmission pulses 1536 by a designated value (or to a designated value).

The electronic device 101 may adjust the reception gain 1538 and/or the sampling rate 1540 of the UWB communication circuit 200 based on the coverage 1526*b* and/or the signal quality 1526*c*. In an embodiment, when the signal acquisition rate indicated by the coverage 1526*b* is low (e.g., less than a designated threshold) or when the signal quality 1526*c* is low (e.g., less than a designated threshold), the electronic device 101 may increase the reception gain 1538 by a designated value (or to a designated value). In an embodiment, when the signal acquisition rate indicated by the coverage 1526*b* is low (e.g., less than a designated threshold) or when the signal quality 1526*c* is low (e.g., less than a designated threshold), the electronic device 101 may increase the sampling rate 1540 by a designated value (or to a designated value).

The electronic device 101 may adjust the number of transmission antennas and/or the number of reception antennas to be included in at least one antenna combination based on at least one of the number of persons 1526*a*, the coverage 1526*b*, the signal quality 1526*c*, the mounting type 1530*a*, or the mounting angle 1530*b*. In an embodiment, when the signal quality 1526*c* is low (e.g., less than a designated threshold), or when the signal acquisition rate indicated by the coverage 1526*b* is low (e.g., less than the designated threshold), the electronic device 101 may increase the number of transmission antennas and/or the number of reception antennas to be included in at least one antenna combination by a designated value (or to a designated value). In an embodiment, when the signal quality 1526*c* is high (e.g., greater than a designated threshold), or when the signal acquisition rate indicated by the coverage 1526*b* is high (e.g., greater than a designated threshold), the electronic device 101 may reduce the number of transmission antennas and/or the number of reception antennas to be included in at least one antenna combination by a designated value (or to a designated value).

The electronic device 101 may select at least one antenna combination 1544 to operate in the next time interval based on the mounting type 1530*a* and/or the mounting angle 1530*b*. In an embodiment, the electronic device 101 may select an antenna combination including the transmission antenna and the reception antenna disposed to face the measurement target, and may not select an antenna combination including the transmission antenna or the reception antenna that does not face the measurement target. In an embodiment, the electronic device 101 may select an antenna combination appropriate for collecting the radar signal reflected from the measurement target.

Figure 16A:
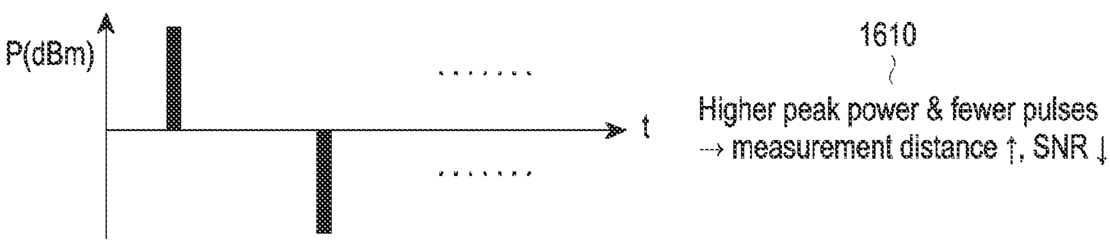
FIGS. 16A and 16B are graphs illustrating adjustment of a measurement distance and SNR according to various embodiments.
Figure 16B:
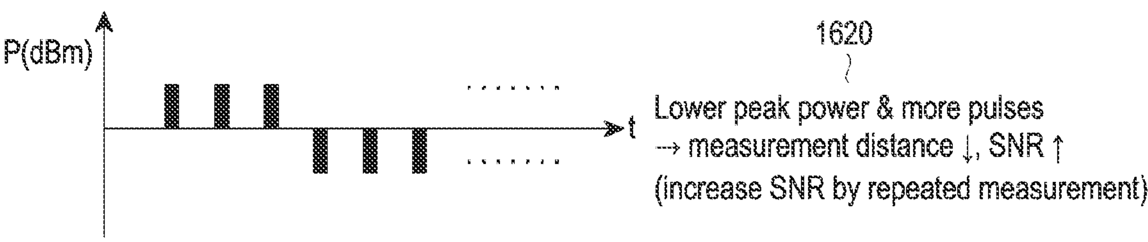

FIGS. 16A and 16B are graphs illustrating adjustment of a measurement distance and SNR according to various embodiments.

Referring to FIG. 16A, under an operating condition 1610 in which transmission power 1534 is high (e.g., greater than a designated threshold) and the number of transmission pulses 1536 is small (e.g., less than a designated threshold), the measurement distance 1532 of the UWB communication circuit 200 may increase and the signal quality 1526*c* may decrease.

Referring to FIG. 16B, under an operating condition 1620 in which transmission power 1534 is low (e.g., less than a designated threshold) and the number of transmission pulses 1536 is large (e.g., greater than a designated threshold), the measurement distance 1532 of the UWB communication circuit 200 may decrease and the signal quality 1526*c* may increase. The electronic device 101 may enhance the signal quality 1526*c* by repeatedly performing measurement through the UWB communication circuit 200.

Figure 17A:
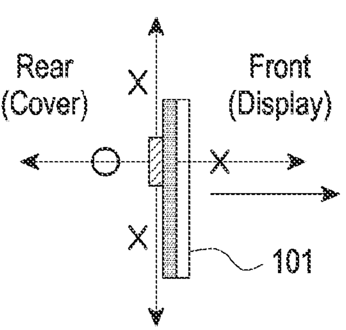
FIGS. 17A and 17B are diagrams illustrating selection of an antenna combination according to various embodiments.
Figure 17A:
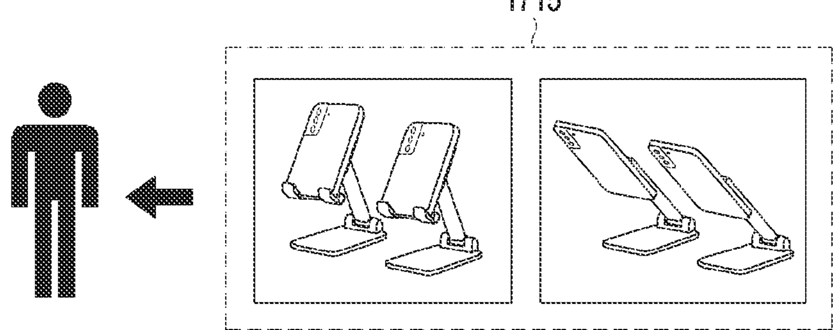
Figure 17B:
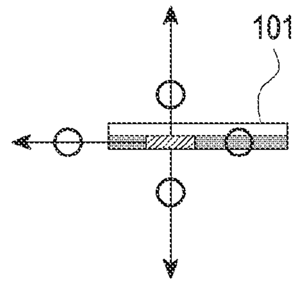
Figure 17B:
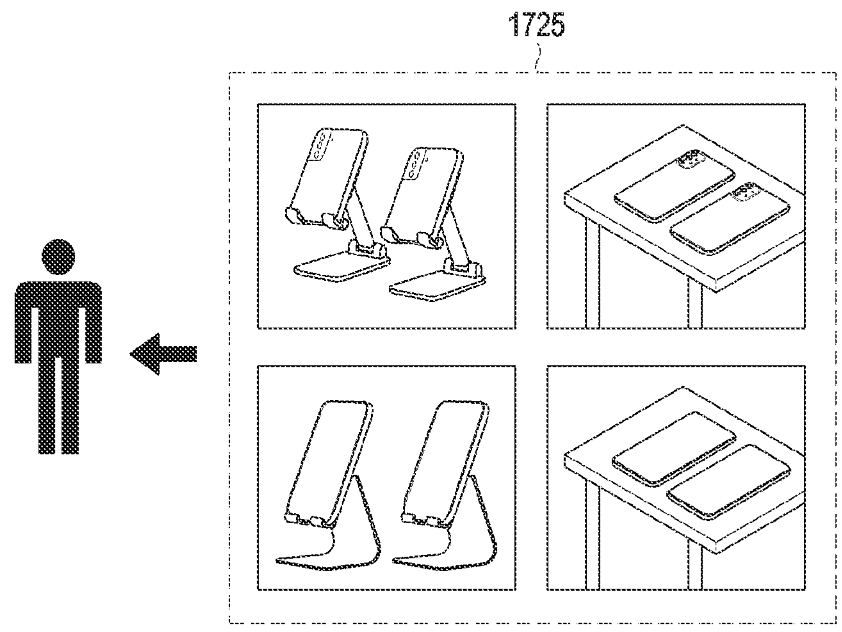

FIGS. 17A and 17B are diagrams illustrating selection of an antenna combination according to various embodiments.

Referring to FIG. 17A, the first antenna combination 1710 may include at least one of ANT1 703, ANT2 705, or ANT3 707. Since ANT1 703, ANT2 705, and ANT3 707 are directional antennas, have excellent transmission performance and reception performance, and are disposed on the rear surface of the electronic device 101, it is impossible to radiate a signal through the front surface of the electronic device 101 on which a display screen is disposed. In the mounting type 1715 (e.g., the mounting type 602 or the mounting type 610) in which the rear surface of the electronic device 101 is disposed to face the measurement target, the electronic device 101 may select a first antenna combination 1710 including at least two of ANT1 703, ANT2 705, or ANT3 707.

Referring to FIG. 17B, the second antenna combination 1720 may include the ANT0 701 and the ANT4 709. Since the ANT0 701 and the ANT4 709 are omnidirectional antennas, the transmission performance and the reception performance are lower than those of the ANT1 703, the ANT2 705, and the ANT3 707, and are disposed on the rear surface of the electronic device 101, signal radiation in all directions of the electronic device 101 is possible. In the mounting type 1725 (e.g., any one of the second mounting type 604, the third mounting type 606, the fourth mounting type 608, or the sixth mounting type 612) in which the side surface of the electronic device 101 may face the measurement target, the electronic device 101 may select the second antenna combination 1720.

An electronic device according to an example embodiment may comprise a sensor module including at least one sensor, a communication circuit including one or more antennas configured to support ultra-wide band (UWB) communication, and at least one processor operatively coupled with the sensor module and the communication circuit. The at least one processor may be configured to identify a mounting state of the electronic device based on sensor data received from the sensor module. The at least one processor may be configured to select at least one antenna combination including at least one transmission antenna and at least one reception antenna from among the one or more antennas according to the mounting state. The at least one processor may be configured to obtain a radar signal related to a measurement target from the communication circuit through the at least one antenna combination. The at least one processor may be configured to obtain a biometric signal from the obtained radar signal. The at least one processor may be configured to evaluate a signal quality of the biometric signal. The at least one processor may be configured to adjust control parameters for an antenna combination selected from among the at least one antenna combination according to the sensor data, the radar signal, and the signal quality of the biometric signal.

In an example embodiment, the at least one processor may be configured to: identify the mounting state including a mounting type and mounting angle of the electronic device based on the sensor data, and select the at least one antenna combination including the at least one transmission antenna and the at least one reception antenna directed toward the measurement target according to the mounting state.

In an example embodiment, the at least one processor may be configured to: determine whether a distance to the measurement target and/or a posture of the measurement target is changed based on the radar signal and the biometric signal, and identify the mounting state of the electronic device based on the distance and/or the posture being changed.

In an example embodiment, the at least one processor may be configured to: determine whether the signal quality of the biometric signal evaluated in a current period is changed from the signal quality in a previous period, and identify the mounting state of the electronic device based on the signal quality being changed.

In an example embodiment, the signal quality may include a signal-to-noise ratio (SNR) and/or autocorrelation value of the biometric signal.

In an example embodiment, the control parameters may include at least one of a measurement distance of the communication circuit, transmission power, a number of transmission pulses, a reception gain, a sampling rate, a number of transmission antennas, or a number of reception antennas.

In an example embodiment, the at least one processor may be configured to: determine a number of at least one person included in the measurement target and a distance to each person based on the radar signal and the biometric signal, and adjust a measurement distance of the communication circuit based on the determined number of the at least one person and distance to each person.

In an example embodiment, the at least one processor may be configured to: determine coverage corresponding to a signal acquisition rate of the communication circuit based on the biometric signal, determine a sleep posture of the measurement target based on the radar signal and the biometric signal, and adjust transmission power of the communication circuit and/or a number of transmission pulses based on the coverage, the signal quality, and the sleep posture.

In an example embodiment, the at least one processor may be configured to: determine coverage corresponding to a signal acquisition rate of the communication circuit based on the biometric signal, and adjust a reception gain of the communication circuit and/or a sampling rate based on the coverage and the signal quality.

In an example embodiment, the at least one processor may be configured to: determine a number of at least one person included in the measurement target based on the radar signal and the biometric signal, determine coverage corresponding to a signal acquisition rate of the communication circuit based on the biometric signal, and adjust a number of transmission antennas and/or a number of reception antennas to be included in the at least one antenna combination based on the number of the at least one person, the coverage, the signal quality, and the mounting type.

A method of operating an electronic device according to an example embodiment may comprise identifying a mounting state of the electronic device based on sensor data received from a sensor module. The method may comprise selecting at least one antenna combination including at least one transmission antenna and at least one reception antenna from among one or more antennas included in an ultra-wideband (UWB) communication circuit according to the mounting state. The method may comprise obtaining a radar signal related to a measurement target from the UWB communication circuit through the at least one antenna combination. The method may comprise obtaining a biometric signal from the obtained radar signal. The method may comprise evaluating a signal quality of the biometric signal. The method may comprise adjusting control parameters for an antenna combination selected from among the at least one antenna combination according to the sensor data, the radar signal, and the signal quality of the biometric signal.

In an example embodiment, the mounting state may include a mounting type and mounting angle of the electronic device. In an embodiment, the selecting may include selecting the at least one antenna combination including the at least one transmission antenna and the at least one reception antenna directed toward the measurement target according to the mounting state.

In an example embodiment, the method may comprise: determining whether a distance to the measurement target and/or a posture of the measurement target is changed based on the radar signal and the biometric signal, and identifying the mounting state of the electronic device based on the distance and/or the posture being changed.

In an example embodiment, the method may comprise: determining whether the signal quality of the biometric signal evaluated in a current period is changed from the signal quality in a previous period, and identifying the mounting state of the electronic device based on the signal quality being changed.

In an example embodiment, the signal quality may include a signal-to-noise ratio (SNR) and/or autocorrelation value of the biometric signal.

In an example embodiment, the control parameters may include at least one of a measurement distance of the communication circuit, transmission power, a number of transmission pulses, a reception gain, a sampling rate, a number of transmission antennas, or a number of reception antennas.

In an example embodiment, the adjusting may include: determining a number of at least one person included in the measurement target and a distance to each person based on the radar signal and the biometric signal, and adjusting a measurement distance of the communication circuit based on the determined number of the at least one person and distance to each person.

In an example embodiment, the adjusting may include: determining coverage corresponding to a signal acquisition rate of the communication circuit based on the biometric signal, determining a sleep posture of the measurement target based on the radar signal and the biometric signal, and adjusting transmission power of the communication circuit and/or a number of transmission pulses based on the coverage, the signal quality, and the sleep posture.

In an example embodiment, the adjusting may include: determining coverage corresponding to a signal acquisition rate of the communication circuit based on the biometric signal, and adjusting a reception gain of the communication circuit and/or a sampling rate based on the coverage and the signal quality.

In an example embodiment, the adjusting may include: determining a number of at least one person included in the measurement target based on the radar signal and the biometric signal, determining coverage corresponding to a signal acquisition rate of the communication circuit based on the biometric signal, and adjusting a number of transmission antennas and/or a number of reception antennas to be included in the at least one antenna combination based on the number of the at least one person, the coverage, the signal quality, and the mounting type.

The electronic device according to various embodiments of the disclosure may be one of various types of electronic devices. The electronic devices may include, for example, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The storage medium readable by the machine may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smartphones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. Some of the plurality of entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various example embodiments, it will be understood that the various example embodiments are intended to be illustrative, not limiting. It will be further understood by those skilled in the art that various changes in form and detail may be made without departing from the true full scope of the disclosure, including the appended claims and their equivalents. It will also be understood that any of the embodiment(s) described herein may be used in conjunction with any other embodiment(s) described herein.

What is claimed is:

1. An electronic device comprising:

a sensor module including at least one sensor;

a communication circuit configured to be connectable to a plurality of antennas, and configured to support ultra-wide band (UWB) communication, wherein the plurality of antennas comprises at least two antennas that are disposed at different positions on and/or inside a housing of the electronic device;

at least one processor, comprising processor circuitry, operatively coupled with the sensor module and the communication circuit; and memory storing instructions, wherein the instructions, when executed by the at least one processor individually and/or collectively, cause the electronic device to:

identify a mounting state of the electronic device based on sensor data received from the sensor module;

based at least in part on positions of the plurality of antennas that are disposed on and/or inside the housing of the electronic device, select at least one antenna combination including at least one transmission antenna and at least one reception antenna from among the plurality of antennas according to the mounting state;

obtain a radar signal related to a measurement target from the communication circuit through the at least one antenna combination;

obtain a biometric signal from the obtained radar signal;

evaluate a signal quality of the biometric signal; and adjust control parameters for an antenna combination selected from among the at least one antenna combination according to the sensor data, the radar signal, and the signal quality of the biometric signal.

2. The electronic device of claim 1, wherein the instructions, when executed by the at least one processor individually and/or collectively, cause the electronic device to:

identify the mounting state including a mounting type and mounting angle of the electronic device based on the sensor data; and select the at least one antenna combination including the at least one transmission antenna and the at least one reception antenna directed toward the measurement target according to the mounting state.

3. The electronic device of claim 1, wherein the instructions, when executed by the at least one processor individually and/or collectively, cause the electronic device to:

determine whether a distance to the measurement target and/or a posture of the measurement target is changed based on changed values of a plurality of radar signals over time and the biometric signal; and identify the mounting state of the electronic device based on the distance and/or the posture being changed.

4. The electronic device of claim 1, wherein the instructions, when executed by the at least one processor individually and/or collectively, cause the electronic device to:

determine whether the signal quality of the biometric signal evaluated in a current period is changed from the signal quality in a previous period; and identify the mounting state of the electronic device based on the signal quality being changed.

5. The electronic device of claim 1, wherein the signal quality includes a signal-to-noise ratio (SNR) and/or autocorrelation value of the biometric signal.

6. The electronic device of claim 1, wherein the control parameters include at least one of a measurement distance of the communication circuit, transmission power, a number of transmission pulses, a reception gain, a sampling rate, a number of transmission antennas, or a number of reception antennas.

7. The electronic device of claim 1, wherein the instructions, when executed by the at least one processor individually and/or collectively, cause the electronic device to:

determine a number of at least one person included in the measurement target and a distance to each person based on the radar signal and the biometric signal; and adjust a measurement distance of the communication circuit based on the determined number of the at least one person and distance to each person.

8. The electronic device of claim 1, wherein the instructions, when executed by the at least one processor individually and/or collectively, cause the electronic device to:

determine coverage corresponding to a signal acquisition rate of the communication circuit based on the biometric signal;

determine a sleep posture of the measurement target based on the radar signal and the biometric signal; and adjust transmission power of the communication circuit and/or a number of transmission pulses based on the coverage, the signal quality, and the sleep posture.

9. The electronic device of claim 1, wherein the instructions, when executed by the at least one processor individually and/or collectively, cause the electronic device to:

determine coverage corresponding to a signal acquisition rate of the communication circuit based on the biometric signal; and adjust a reception gain of the communication circuit and/or a sampling rate based on the coverage and the signal quality.

10. The electronic device of claim 1, wherein the instructions, when executed by the at least one processor individually and/or collectively, cause the electronic device to:

determine a number of at least one person included in the measurement target based on the radar signal and the biometric signal;

determine coverage corresponding to a signal acquisition rate of the communication circuit based on the biometric signal; and adjust a number of transmission antennas and/or a number of reception antennas to be included in the at least one antenna combination based on the number of the at least one person, the coverage, the signal quality, and the mounting type.

11. A method of operating an electronic device, wherein the electronic device includes a communication circuit configured to be connectable to a plurality of antennas, and configured to support ultra-wide band (UWB) communication, the plurality of antennas comprising at least two antennas that are disposed at different positions on and/or inside a housing of the electronic device, comprising:

identifying a mounting state of the electronic device based on sensor data received from a sensor module;

based at least in part on positions of the plurality of antennas that are disposed on and/or inside the housing of the electronic device, selecting at least one antenna combination including at least one transmission antenna and at least one reception antenna from among the plurality of antennas according to the mounting state;

obtaining a radar signal related to a measurement target from the UWB communication circuit through the at least one antenna combination;

obtaining a biometric signal from the obtained radar signal;

evaluating a signal quality of the biometric signal; and adjusting control parameters for an antenna combination selected from among the at least one antenna combination according to the sensor data, the radar signal, and the signal quality of the biometric signal.

12. The method of claim 11, wherein the mounting state includes a mounting type and mounting angle of the electronic device, and wherein the selecting includes selecting the at least one antenna combination including the at least one transmission antenna and the at least one reception antenna directed toward the measurement target according to the mounting state.

13. The method of claim 11, further comprising:

determining whether a distance to the measurement target and/or a posture of the measurement target is changed based on changed values of a plurality of radar signals over time and the biometric signal; and identifying the mounting state of the electronic device based on the distance and/or the posture being changed.

14. The method of claim 11, further comprising:

determining whether the signal quality of the biometric signal evaluated in a current period is changed from the signal quality in a previous period; and identifying the mounting state of the electronic device based on the signal quality being changed.

15. The method of claim 11, wherein the signal quality includes a signal-to-noise ratio (SNR) and/or autocorrelation value of the biometric signal.

16. The method of claim 11, wherein the control parameters include at least one of a measurement distance of the communication circuit, transmission power, a number of transmission pulses, a reception gain, a sampling rate, a number of transmission antennas, or a number of reception antennas.

17. The method of claim 11, wherein the adjusting includes:

determining a number of at least one person included in the measurement target and a distance to each person based on the radar signal and the biometric signal; and adjusting a measurement distance of the communication circuit based on the determined number of the at least one person and distance to each person.

18. The method of claim 11, wherein the adjusting includes:

determining coverage corresponding to a signal acquisition rate of the communication circuit based on the biometric signal;

determining a sleep posture of the measurement target based on the radar signal and the biometric signal; and adjusting transmission power of the communication circuit and/or a number of transmission pulses based on the coverage, the signal quality, and the sleep posture.

19. The method of claim 11, wherein the adjusting includes:

determining coverage corresponding to a signal acquisition rate of the communication circuit based on the biometric signal; and adjusting a reception gain of the communication circuit and/or a sampling rate based on the coverage and the signal quality.

20. The method of claim 11, wherein the adjusting includes:

determining a number of at least one person included in the measurement target based on the radar signal and the biometric signal;

determining coverage corresponding to a signal acquisition rate of the communication circuit based on the biometric signal; and adjusting a number of transmission antennas and/or a number of reception antennas to be included in the at least one antenna combination based on the number of the at least one person, the coverage, the signal quality, and the mounting type.

* * * * *